US006710027B2

(12) United States Patent
Bradfisch et al.

(10) Patent No.: US 6,710,027 B2
(45) Date of Patent: Mar. 23, 2004

(54) *BACILLUS THURINGIENSIS* TOXINS AND GENES FOR CONTROLLING COLEOPTERAN PESTS

(75) Inventors: Gregory A. Bradfisch, San Diego, CA (US); Judy Muller-Cohn, Del Mar, CA (US); Kenneth E. Narva, San Diego, CA (US); Jenny M. Fu, San Diego, CA (US); Mark Thompson, San Diego, CA (US)

(73) Assignee: Mycogen Corporation, Indianapolis, IN (US)

(*) Notice: Subject to any disclaimer, the term of this patent is extended or adjusted under 35 U.S.C. 154(b) by 17 days.

(21) Appl. No.: 09/991,582

(22) Filed: Nov. 16, 2001

(65) Prior Publication Data

US 2004/0006785 A1 Jan. 8, 2004

Related U.S. Application Data

(60) Division of application No. 09/307,925, filed on May 10, 1999, now Pat. No. 6,344,553, which is a continuation-in-part of application No. 09/076,193, filed on May 12, 1998, now Pat. No. 5,973,231.

(51) Int. Cl.$^7$ .............................................. A01N 37/18

(52) U.S. Cl. ............................. 514/2; 530/50; 530/300

(58) Field of Search ................................ 530/300, 350; 514/2, 12; 536/23, 71; 435/252.3, 419, 243, 69.1

(56) References Cited

U.S. PATENT DOCUMENTS

| | | | |
|---|---|---|---|
| 4,448,885 A | | 5/1984 | Schnepf et al. |
| 4,467,036 A | | 8/1984 | Schnepf et al. |
| 4,764,372 A | | 8/1988 | Herrnstadt et al. |
| 4,797,276 A | | 1/1989 | Herrnstadt et al. |
| 4,849,217 A | | 7/1989 | Soares et al. |
| 4,853,331 A | | 8/1989 | Herrnstadt et al. |
| 4,861,595 A | | 8/1989 | Barnes et al. |
| 4,918,006 A | | 4/1990 | Ellar et al. |
| 4,948,734 A | | 8/1990 | Edwards et al. |
| 4,966,765 A | | 10/1990 | Payne et al. |
| 4,990,332 A | | 2/1991 | Payne et al. |
| 4,996,155 A | | 2/1991 | Sick et al. |
| 5,039,523 A | | 8/1991 | Payne et al. |
| 5,093,120 A | | 3/1992 | Edwards et al. |
| 5,126,133 A | | 6/1992 | Payne et al. |
| 5,151,363 A | | 9/1992 | Payne |
| 5,186,934 A | | 2/1993 | Narva et al. |
| 5,208,017 A | | 5/1993 | Bradfisch et al. |
| 5,236,843 A | | 8/1993 | Narva et al. |
| 5,262,158 A | | 11/1993 | Payne et al. |
| 5,262,159 A | | 11/1993 | Payne et al. |
| 5,262,399 A | | 11/1993 | Hickle et al. |
| 5,273,746 A | | 12/1993 | Payne et al. |
| 5,275,815 A | | 1/1994 | Payne |
| 5,286,485 A | | 2/1994 | Uyeda et al. |
| 5,298,245 A | | 3/1994 | Payne et al. |
| 5,322,932 A | | 6/1994 | Narva et al. |
| 5,380,831 A | | 1/1995 | Adang et al. |
| 5,424,410 A | | 6/1995 | Payne et al. |
| 5,427,786 A | | 6/1995 | Payne et al. |
| 5,439,881 A | | 8/1995 | Narva et al. |
| 5,468,636 A | | 11/1995 | Payne et al. |
| 5,670,365 A | | 9/1997 | Feitelson |
| 6,071,511 A | * | 6/2000 | Payne et al. ............... 424/93.2 |

FOREIGN PATENT DOCUMENTS

| | | |
|---|---|---|
| EP | 0 462 721 | 12/1991 |
| WO | WO 92/19739 | 11/1992 |
| WO | WO 93/04587 | 3/1993 |
| WO | WO 93/14641 | 8/1993 |
| WO | WO 94/23036 | 10/1994 |
| WO | WO 95/02694 | 1/1995 |

OTHER PUBLICATIONS

Beegle, C.C., "Use Entomogenous Bacteria in Agroecosystems," *Developments in Industrial Microbiology,* 1978, pp. 97–104, vol. 20.

Couch, T.L., "Mosquito Pathogenicity of *Bacillus thuringiensis* var. *israelensis*," *Developments in Industrial Mirobiology,* 1980, pp. 61–76, vol. 22.

Crickmore, N. et al., Society for Invertebrate Pathology 29$^{th}$ Annual Meeting, 3$^{rd}$ International Colloquium on *Bacills thuringiensis,* University of Cordoba, Sep. 1–6, 1996, Abstract.

Feitelson, J.S. et al., "*Bacillus thuringiensis*: Insects and Beyond," *Biotechnology,* 1992, pp. 271–275, vol. 10.

Gaertner, F.H. and Leo Kim, "Current Applied Recombinant DNA Projects," *TIBTECH,* 1988, pp. 54–57, vol. 6(4).

Gaertner, F.H., "Cellular Delivery Systems for Insecticidal Proteins: Living and Non–Living Microorganisms," *Controlled Delivery of Crop Protection Agents*, R.M. Wilkins, ed., 1989, pp. 245–255, Taylor and Francis, New York and London.

Hofte, H. and H.R. Whiteley, "Insecticidal Crystal Proteins of *Bacillus thuringiensis," Microbiological Reviews,* 1989, pp. 242–255, vol. 53(2).

(List continued on next page.)

*Primary Examiner*—Karen Cochrane Carlson
*Assistant Examiner*—Sheridan Snedden
(74) *Attorney, Agent, or Firm*—Saliwanchik, Lloyd & Saliwanchik

(57) ABSTRACT

The subject invention concerns materials and methods useful in the control of pests and, particularly, plant pests. More specifically, the subject invention concerns novel genes and pesticidal toxins referred to as 86A1(b) and 52A1(b). In preferred embodiments, the subject toxins are used for controlling flea beetles of the genus Phyllotreta. Using the genes described herein, the transformation of plants can be accomplished using techniques known to those skilled in the art. In addition, the subject invention provides toxin genes optimized for expression in plants.

10 Claims, No Drawings

OTHER PUBLICATIONS

Krieg, V.A. et al. "*Bacillus thuringiensis* var. *tenebrionis,* a new pathotype effective against larvae of Coleoptera," *Z. Ang. Ent.,* 1983, pp. 500–508, vol. 96.

Schnepf, H.E. and H.R. Whiteley, "Cloning and Expression of the *Bacillus thuringiensis* Crystal Protein Gene in *Escherichia coli," Proc. Natl. Acad. Sci. USA,* 1981, pp. 2893–2897, vol. 78(5).

Schnepf, H.E., "B.t. toxins: regulation, activities and structural diversity," *Current Opinion Biotech,* 1995, pp. 305–312, vol. 6.

Vaeck et al., "Transgenic Plants Protected from Insect Attack," *Nature,* 1987, pp. 33–37, vol. 328.

* cited by examiner

SEQUENCE LISTING

```
<160> NUMBER OF SEQ ID NOS: 19

<210> SEQ ID NO 1
<211> LENGTH: 40
<212> TYPE: DNA
<213> ORGANISM: Forward probe

<400> SEQUENCE: 1

tggataaaaa atcwatwaca catgaagaat ttatwmgaca                         40


<210> SEQ ID NO 2
<211> LENGTH: 1089
<212> TYPE: DNA
<213> ORGANISM: Bacillus thuringiensis strain PS86A1

<400> SEQUENCE: 2

ttgaacaaaa aatctattac tcatgaagaa tttattagac aattaaaaga atataattta     60

gataacaatc ttaattatca tgatccagct gtactaaaaa aaattaatga attattacct    120

gctgatcaac aatatgattt aatttcaccc actcaagatt ggtatcaatt taaaacttta    180

tatcctattt ctaagaatgg tgtaattatt tcatctaatc tagatgatag ctcaaacgtt    240

ctagtcccag aattatctga aaatccttat gatccaattc cccaatcagg taagtcaaca    300

attcaaactg ctgtacgttc accagaagct ctttatatta ttctaactac taacaacagt    360

ctatcttttg gtgatggtac caatggaatg atagcagcac gtatagcatt attaagtgtg    420

actcgcccag aactttctca agcaattaca aaagtaaatt acgtttataa atcaggacaa    480

acagctccta gaaatgctcc tgtagcatat attgaactat ctccaaataa tagttatgta    540

caaactcttt taaatgatag tcatatgaaa cgaacatctt catacgaact cgttggatct    600

agcatagcaa gaagaggaat tgaaacaaaa tggagtaaat ctcatacctc tggtgtaagt    660

gatacagata gttggtcact agcagtatct gctggtattg atattgaatg ggatgtaggt    720

attccactta ctgcttctgc aaaagaaaaa ttatctctca gtataactgg aacatatggt    780

caatctacta cagtatcatc tcaagataca attacacaag aatatacttt tgctaagcca    840

ggaaaagatt ataaatatga tgattatgct tatgctgtat atcaattaaa atctaattat    900

caattcatag ctggagatgc ttttaataat ttaataaatt ctctatcatt tggtaatcag    960

tttagtgtac atggagatgc aagctatcaa tatagtacag atacaatttt tagcactcaa   1020

acacctgatc caacaccaac aaatgaaaag tcattaattc aggtaaattt taatcctaga   1080

ttttcataa                                                            1089
```

-continued

```
<210> SEQ ID NO 3
<211> LENGTH: 362
<212> TYPE: PRT
<213> ORGANISM: Bacillus thuringiensis strain PS86A1

<400> SEQUENCE: 3

Leu Asn Lys Lys Ser Ile Thr His Glu Glu Phe Ile Arg Gln Leu Lys
1               5                   10                  15

Glu Tyr Asn Leu Asp Asn Asn Leu Asn Tyr His Asp Pro Ala Val Leu
            20                  25                  30

Lys Lys Ile Asn Glu Leu Leu Pro Ala Asp Gln Gln Tyr Asp Leu Ile
        35                  40                  45

Ser Pro Thr Gln Asp Trp Tyr Gln Phe Lys Thr Leu Tyr Pro Ile Ser
    50                  55                  60

Lys Asn Gly Val Ile Ile Ser Ser Asn Leu Asp Asp Ser Ser Asn Val
65                  70                  75                  80

Leu Val Pro Glu Leu Ser Glu Asn Pro Tyr Asp Pro Ile Pro Gln Ser
                85                  90                  95

Gly Lys Ser Thr Ile Gln Thr Ala Val Arg Ser Pro Glu Ala Leu Tyr
            100                 105                 110

Ile Ile Leu Thr Thr Asn Asn Ser Leu Ser Phe Gly Asp Gly Thr Asn
        115                 120                 125

Gly Met Ile Ala Ala Arg Ile Ala Leu Leu Ser Val Thr Arg Pro Glu
    130                 135                 140

Leu Ser Gln Ala Ile Thr Lys Val Asn Tyr Val Tyr Lys Ser Gly Gln
145                 150                 155                 160

Thr Ala Pro Arg Asn Ala Pro Val Ala Tyr Ile Glu Leu Ser Pro Asn
                165                 170                 175

Asn Ser Tyr Val Gln Thr Leu Leu Asn Asp Ser His Met Lys Arg Thr
            180                 185                 190

Ser Ser Tyr Glu Leu Val Gly Ser Ser Ile Ala Arg Arg Gly Ile Glu
        195                 200                 205

Thr Lys Trp Ser Lys Ser His Thr Ser Gly Val Ser Asp Thr Asp Ser
    210                 215                 220

Trp Ser Leu Ala Val Ser Ala Gly Ile Asp Ile Glu Trp Asp Val Gly
225                 230                 235                 240

Ile Pro Leu Thr Ala Ser Ala Lys Glu Lys Leu Ser Leu Ser Ile Thr
                245                 250                 255

Gly Thr Tyr Gly Gln Ser Thr Thr Val Ser Ser Gln Asp Thr Ile Thr
            260                 265                 270

Gln Glu Tyr Thr Phe Ala Lys Pro Gly Lys Asp Tyr Lys Tyr Asp Asp
        275                 280                 285

Tyr Ala Tyr Ala Val Tyr Gln Leu Lys Ser Asn Tyr Gln Phe Ile Ala
    290                 295                 300

Gly Asp Ala Phe Asn Asn Leu Ile Asn Ser Leu Ser Phe Gly Asn Gln
305                 310                 315                 320

Phe Ser Val His Gly Asp Ala Ser Tyr Gln Tyr Ser Thr Asp Thr Ile
                325                 330                 335

Phe Ser Thr Gln Thr Pro Asp Pro Thr Pro Thr Asn Glu Lys Ser Leu
            340                 345                 350

Ile Gln Val Asn Phe Asn Pro Arg Phe Ser
        355                 360

<210> SEQ ID NO 4
<211> LENGTH: 1089
```

-continued

<212> TYPE: DNA
<213> ORGANISM: Bacillus thuringiensis strain PS52A1

<400> SEQUENCE: 4
ttgaacaaaa aatctattac tcatgaagaa tttattagac aattaaaaga atataattta 60
gataacaatc ttaattatca tgatccagct gtactaaaaa aaattaatga attattacct 120
gctgatcaac aatatgattt aatttcaccc actcaagatt ggtatcaatt taaaacttta 180
tatcctattt ctaagaatgg tgtaattatt tcatctaatc tagatgatag ctcaaacgtt 240
ctagtcccag aattatctga aaatccttat gatccaattc cccaatcagg taagtcaaca 300
attcaaactg ctgtacgttc accagaagct ctttatatta ttctaactac taacaacagt 360
ctatcttttg gtggtggtac caatacaatg atagcaacac gtatagcatt attaagtgtg 420
actcgcccag aactttatca agcaattaca aaagtaaatt acgtttataa atcaggacaa 480
acagctccta gaaatgctcc tgtagcatat attgaactat ctccaaataa tagttatgta 540
caaactcttt taaatgatag tcatatgaaa cgaacatctt catacgaact cgttggatct 600
agcatagcaa gaagaggaat tgaaacaaaa tggagtaaat ctcatacctc tggtgtaagt 660
gatacagata gttggtcact agcagtatct gctggtattg atattgaatg ggatgtaggt 720
attccactta ctgcttctgc aaaagaaaaa ttatctctca gtataactgg aacatatggt 780
caatctacta cagtatcatc tcaagataca attacacaag aatatacttt tgctaagcca 840
ggaaaagatt ataaatatga tgattatgct tatgctgtat atcaattaaa atctaattat 900
caattcatag ctggagatgc ttttaataat ttaataaatt ctctatcatt tggtaatcag 960
tttagtgtac atggagatgc aagctatcaa tatagtacag atacaatttt tagcactcaa 1020
acacctgatc caacaccaac aaatgaaaag tcattaattc aggtaaattt taatcctaga 1080
ttttcataa 1089

<210> SEQ ID NO 5
<211> LENGTH: 362
<212> TYPE: PRT
<213> ORGANISM: Bacillus thuringiensis strain PS52A1

<400> SEQUENCE: 5

```
Leu Asn Lys Lys Ser Ile Thr His Glu Glu Phe Ile Arg Gln Leu Lys
1               5                   10                  15

Glu Tyr Asn Leu Asp Asn Asn Leu Asn Tyr His Asp Pro Ala Val Leu
            20                  25                  30

Lys Lys Ile Asn Glu Leu Leu Pro Ala Asp Gln Gln Tyr Asp Leu Ile
        35                  40                  45

Ser Pro Thr Gln Asp Trp Tyr Gln Phe Lys Thr Leu Tyr Pro Ile Ser
    50                  55                  60

Lys Asn Gly Val Ile Ile Ser Ser Asn Leu Asp Asp Ser Ser Asn Val
65                  70                  75                  80

Leu Val Pro Glu Leu Ser Glu Asn Pro Tyr Asp Pro Ile Pro Gln Ser
                85                  90                  95

Gly Lys Ser Thr Ile Gln Thr Ala Val Arg Ser Pro Glu Ala Leu Tyr
            100                 105                 110

Ile Ile Leu Thr Thr Asn Asn Ser Leu Ser Phe Gly Gly Gly Thr Asn
        115                 120                 125

Thr Met Ile Ala Thr Arg Ile Ala Leu Leu Ser Val Thr Arg Pro Glu
    130                 135                 140

Leu Tyr Gln Ala Ile Thr Lys Val Asn Tyr Val Tyr Lys Ser Gly Gln
```

-continued

```
145                 150                 155                 160

Thr Ala Pro Arg Asn Ala Pro Val Ala Tyr Ile Glu Leu Ser Pro Asn
                165                 170                 175

Asn Ser Tyr Val Gln Thr Leu Leu Asn Asp Ser His Met Lys Arg Thr
            180                 185                 190

Ser Ser Tyr Glu Leu Val Gly Ser Ser Ile Ala Arg Arg Gly Ile Glu
        195                 200                 205

Thr Lys Trp Ser Lys Ser His Thr Ser Gly Val Ser Asp Thr Asp Ser
    210                 215                 220

Trp Ser Leu Ala Val Ser Ala Gly Ile Asp Ile Glu Trp Asp Val Gly
225                 230                 235                 240

Ile Pro Leu Thr Ala Ser Ala Lys Glu Lys Leu Ser Leu Ser Ile Thr
                245                 250                 255

Gly Thr Tyr Gly Gln Ser Thr Thr Val Ser Ser Gln Asp Thr Ile Thr
            260                 265                 270

Gln Glu Tyr Thr Phe Ala Lys Pro Gly Lys Asp Tyr Lys Tyr Asp Asp
        275                 280                 285

Tyr Ala Tyr Ala Val Tyr Gln Leu Lys Ser Asn Tyr Gln Phe Ile Ala
    290                 295                 300

Gly Asp Ala Phe Asn Asn Leu Ile Asn Ser Leu Ser Phe Gly Asn Gln
305                 310                 315                 320

Phe Ser Val His Gly Asp Ala Ser Tyr Gln Tyr Ser Thr Asp Thr Ile
                325                 330                 335

Phe Ser Thr Gln Thr Pro Asp Pro Thr Pro Thr Asn Glu Lys Ser Leu
            340                 345                 350

Ile Gln Val Asn Phe Asn Pro Arg Phe Ser
        355                 360
```

<210> SEQ ID NO 6
<211> LENGTH: 1086
<212> TYPE: DNA
<213> ORGANISM: Bacillus thuringiensis clone MR510

<400> SEQUENCE: 6

```
atgaacaaga agtctatcac tcatgaggag ttcatcagac aactcaagga atacaacctt     60

gacaacaacc tcaactacca tgatccagct gttctcaaga agatcaacga gcttcttcca    120

gctgatcaac agtacgatct catctctcca actcaagatt ggtaccaatt caagactctc    180

tacccaatct ctaagaacgg agtgatcatc tcttctaacc ttgatgattc ttctaacgtt    240

cttgttccag agctttctga gaacccatac gatccaatcc cacaatctgg aaagtctact    300

atccaaactg ctgttagatc tccagaggct ctctacatca ttcttactac taacaactct    360

ctttctttcg gaggtggaac taacactatg attgctacta gaatcgctct tctttctgtt    420

actagaccag agctctatca agctatcact aaggtgaact acgtgtacaa gtctggacaa    480

actgctccaa gaaacgctcc agttgcttac attgagcttt ctccaaacaa ctcttacgtt    540

caaactcttc tcaacgattc tcacatgaag agaactagtt cttacgagct tgttggatct    600

tctatcgcta gaagaggaat cgagactaag tggtctaagt ctcatacttc tggagtttct    660

gatactgatt cttggtctct tgctgtttct gctggaatcg acattgaatg ggatgttgga    720

atcccactta ctgcttctgc taaggagaag ctttctcttt ctatcactgg aacttacgga    780

caatctacta ctgtttcttc tcaagatact atcactcaag agtacacttt cgctaagcca    840

ggaaaggact acaaatacga tgactacgct tacgctgtgt accaactcaa gagcaactat    900
```

-continued

```
cagttcattg ctggagatgc attcaacaac ctcatcaact ctctttcttt cggaaaccag    960

ttctctgttc atggagatgc ttcttaccag tactctactg atactatctt ctctactcaa   1020

actccagatc caactccaac taacgagaag tctctcattc aagtgaactt caacccaaga   1080

ttctct                                                              1086


<210> SEQ ID NO 7
<211> LENGTH: 362
<212> TYPE: PRT
<213> ORGANISM: Bacillus thuringiensis clone MR510

<400> SEQUENCE: 7

Met Asn Lys Lys Ser Ile Thr His Glu Glu Phe Ile Arg Gln Leu Lys
1               5                   10                  15

Glu Tyr Asn Leu Asp Asn Asn Leu Asn Tyr His Asp Pro Ala Val Leu
            20                  25                  30

Lys Lys Ile Asn Glu Leu Leu Pro Ala Asp Gln Gln Tyr Asp Leu Ile
        35                  40                  45

Ser Pro Thr Gln Asp Trp Tyr Gln Phe Lys Thr Leu Tyr Pro Ile Ser
    50                  55                  60

Lys Asn Gly Val Ile Ile Ser Ser Asn Leu Asp Asp Ser Ser Asn Val
65                  70                  75                  80

Leu Val Pro Glu Leu Ser Glu Asn Pro Tyr Asp Pro Ile Pro Gln Ser
                85                  90                  95

Gly Lys Ser Thr Ile Gln Thr Ala Val Arg Ser Pro Glu Ala Leu Tyr
            100                 105                 110

Ile Ile Leu Thr Thr Asn Asn Ser Leu Ser Phe Gly Gly Gly Thr Asn
        115                 120                 125

Thr Met Ile Ala Thr Arg Ile Ala Leu Leu Ser Val Thr Arg Pro Glu
    130                 135                 140

Leu Tyr Gln Ala Ile Thr Lys Val Asn Tyr Val Tyr Lys Ser Gly Gln
145                 150                 155                 160

Thr Ala Pro Arg Asn Ala Pro Val Ala Tyr Ile Glu Leu Ser Pro Asn
                165                 170                 175

Asn Ser Tyr Val Gln Thr Leu Leu Asn Asp Ser His Met Lys Arg Thr
            180                 185                 190

Ser Ser Tyr Glu Leu Val Gly Ser Ser Ile Ala Arg Arg Gly Ile Glu
        195                 200                 205

Thr Lys Trp Ser Lys Ser His Thr Ser Gly Val Ser Asp Thr Asp Ser
    210                 215                 220

Trp Ser Leu Ala Val Ser Ala Gly Ile Asp Ile Glu Trp Asp Val Gly
225                 230                 235                 240

Ile Pro Leu Thr Ala Ser Ala Lys Glu Lys Leu Ser Leu Ser Ile Thr
                245                 250                 255

Gly Thr Tyr Gly Gln Ser Thr Thr Val Ser Ser Gln Asp Thr Ile Thr
            260                 265                 270

Gln Glu Tyr Thr Phe Ala Lys Pro Gly Lys Asp Tyr Lys Tyr Asp Asp
        275                 280                 285

Tyr Ala Tyr Ala Val Tyr Gln Leu Lys Ser Asn Tyr Gln Phe Ile Ala
    290                 295                 300

Gly Asp Ala Phe Asn Asn Leu Ile Asn Ser Leu Ser Phe Gly Asn Gln
305                 310                 315                 320

Phe Ser Val His Gly Asp Ala Ser Tyr Gln Tyr Ser Thr Asp Thr Ile
                325                 330                 335
```

-continued

```
Phe Ser Thr Gln Thr Pro Asp Pro Thr Pro Thr Asn Glu Lys Ser Leu
            340                 345                 350

Ile Gln Val Asn Phe Asn Pro Arg Phe Ser
        355                 360


<210> SEQ ID NO 8
<211> LENGTH: 354
<212> TYPE: PRT
<213> ORGANISM: Artificial Sequence
<220> FEATURE:
<223> OTHER INFORMATION: Truncated protein

<400> SEQUENCE: 8

Met Glu Phe Ile Arg Gln Leu Lys Glu Tyr Asn Leu Asp Asn Asn Leu
1               5                   10                  15

Asn Tyr His Asp Pro Ala Val Leu Lys Lys Ile Asn Glu Leu Leu Pro
            20                  25                  30

Ala Asp Gln Gln Tyr Asp Leu Ile Ser Pro Thr Gln Asp Trp Tyr Gln
        35                  40                  45

Phe Lys Thr Leu Tyr Pro Ile Ser Lys Asn Gly Val Ile Ile Ser Ser
    50                  55                  60

Asn Leu Asp Asp Ser Ser Asn Val Leu Val Pro Glu Leu Ser Glu Asn
65                  70                  75                  80

Pro Tyr Asp Pro Ile Pro Gln Ser Gly Lys Ser Thr Ile Gln Thr Ala
                85                  90                  95

Val Arg Ser Pro Glu Ala Leu Tyr Ile Ile Leu Thr Thr Asn Asn Ser
            100                 105                 110

Leu Ser Phe Gly Gly Gly Thr Asn Thr Met Ile Ala Thr Arg Ile Ala
        115                 120                 125

Leu Leu Ser Val Thr Arg Pro Glu Leu Tyr Gln Ala Ile Thr Lys Val
    130                 135                 140

Asn Tyr Val Tyr Lys Ser Gly Gln Thr Ala Pro Arg Asn Ala Pro Val
145                 150                 155                 160

Ala Tyr Ile Glu Leu Ser Pro Asn Asn Ser Tyr Val Gln Thr Leu Leu
                165                 170                 175

Asn Asp Ser His Met Lys Arg Thr Ser Ser Tyr Glu Leu Val Gly Ser
            180                 185                 190

Ser Ile Ala Arg Arg Gly Ile Glu Thr Lys Trp Ser Lys Ser His Thr
        195                 200                 205

Ser Gly Val Ser Asp Thr Asp Ser Trp Ser Leu Ala Val Ser Ala Gly
    210                 215                 220

Ile Asp Ile Glu Trp Asp Val Gly Ile Pro Leu Thr Ala Ser Ala Lys
225                 230                 235                 240

Glu Lys Leu Ser Leu Ser Ile Thr Gly Thr Tyr Gly Gln Ser Thr Thr
                245                 250                 255

Val Ser Ser Gln Asp Thr Ile Thr Gln Glu Tyr Thr Phe Ala Lys Pro
            260                 265                 270

Gly Lys Asp Tyr Lys Tyr Asp Asp Tyr Ala Tyr Ala Val Tyr Gln Leu
        275                 280                 285

Lys Ser Asn Tyr Gln Phe Ile Ala Gly Asp Ala Phe Asn Asn Leu Ile
    290                 295                 300

Asn Ser Leu Ser Phe Gly Asn Gln Phe Ser Val His Gly Asp Ala Ser
305                 310                 315                 320

Tyr Gln Tyr Ser Thr Asp Thr Ile Phe Ser Thr Gln Thr Pro Asp Pro
                325                 330                 335
```

-continued

```
Thr Pro Thr Asn Glu Lys Ser Leu Ile Gln Val Asn Phe Asn Pro Arg
            340                 345                 350

Phe Ser


<210> SEQ ID NO 9
<211> LENGTH: 343
<212> TYPE: PRT
<213> ORGANISM: Artificial sequence
<220> FEATURE:
<223> OTHER INFORMATION: Truncated protein

<400> SEQUENCE: 9

Met Asp Asn Asn Leu Asn Tyr His Asp Pro Ala Val Leu Lys Lys Ile
1               5                   10                  15

Asn Glu Leu Leu Pro Ala Asp Gln Gln Tyr Asp Leu Ile Ser Pro Thr
            20                  25                  30

Gln Asp Trp Tyr Gln Phe Lys Thr Leu Tyr Pro Ile Ser Lys Asn Gly
        35                  40                  45

Val Ile Ile Ser Ser Asn Leu Asp Asp Ser Ser Asn Val Leu Val Pro
    50                  55                  60

Glu Leu Ser Glu Asn Pro Tyr Asp Pro Ile Pro Gln Ser Gly Lys Ser
65                  70                  75                  80

Thr Ile Gln Thr Ala Val Arg Ser Pro Glu Ala Leu Tyr Ile Ile Leu
                85                  90                  95

Thr Thr Asn Asn Ser Leu Ser Phe Gly Gly Gly Thr Asn Thr Met Ile
            100                 105                 110

Ala Thr Arg Ile Ala Leu Leu Ser Val Thr Arg Pro Glu Leu Tyr Gln
        115                 120                 125

Ala Ile Thr Lys Val Asn Tyr Val Tyr Lys Ser Gly Gln Thr Ala Pro
    130                 135                 140

Arg Asn Ala Pro Val Ala Tyr Ile Glu Leu Ser Pro Asn Asn Ser Tyr
145                 150                 155                 160

Val Gln Thr Leu Leu Asn Asp Ser His Met Lys Arg Thr Ser Ser Tyr
                165                 170                 175

Glu Leu Val Gly Ser Ser Ile Ala Arg Arg Gly Ile Glu Thr Lys Trp
            180                 185                 190

Ser Lys Ser His Thr Ser Gly Val Ser Asp Thr Asp Ser Trp Ser Leu
        195                 200                 205

Ala Val Ser Ala Gly Ile Asp Ile Glu Trp Asp Val Gly Ile Pro Leu
    210                 215                 220

Thr Ala Ser Ala Lys Glu Lys Leu Ser Leu Ser Ile Thr Gly Thr Tyr
225                 230                 235                 240

Gly Gln Ser Thr Thr Val Ser Ser Gln Asp Thr Ile Thr Gln Glu Tyr
                245                 250                 255

Thr Phe Ala Lys Pro Gly Lys Asp Tyr Lys Tyr Asp Asp Tyr Ala Tyr
            260                 265                 270

Ala Val Tyr Gln Leu Lys Ser Asn Tyr Gln Phe Ile Ala Gly Asp Ala
        275                 280                 285

Phe Asn Asn Leu Ile Asn Ser Leu Ser Phe Gly Asn Gln Phe Ser Val
    290                 295                 300

His Gly Asp Ala Ser Tyr Gln Tyr Ser Thr Asp Thr Ile Phe Ser Thr
305                 310                 315                 320

Gln Thr Pro Asp Pro Thr Pro Thr Asn Glu Lys Ser Leu Ile Gln Val
                325                 330                 335

Asn Phe Asn Pro Arg Phe Ser
```

-continued

340

<210> SEQ ID NO 10
<211> LENGTH: 337
<212> TYPE: PRT
<213> ORGANISM: Artificial sequence
<220> FEATURE:
<223> OTHER INFORMATION: Truncated protein

<400> SEQUENCE: 10

```
Met His Asp Pro Ala Val Leu Lys Lys Ile Asn Glu Leu Leu Pro Ala
1               5                   10                  15

Asp Gln Gln Tyr Asp Leu Ile Ser Pro Thr Gln Asp Trp Tyr Gln Phe
            20                  25                  30

Lys Thr Leu Tyr Pro Ile Ser Lys Asn Gly Val Ile Ile Ser Ser Asn
        35                  40                  45

Leu Asp Asp Ser Ser Asn Val Leu Val Pro Glu Leu Ser Glu Asn Pro
    50                  55                  60

Tyr Asp Pro Ile Pro Gln Ser Gly Lys Ser Thr Ile Gln Thr Ala Val
65                  70                  75                  80

Arg Ser Pro Glu Ala Leu Tyr Ile Ile Leu Thr Thr Asn Asn Ser Leu
                85                  90                  95

Ser Phe Gly Gly Gly Thr Asn Thr Met Ile Ala Thr Arg Ile Ala Leu
            100                 105                 110

Leu Ser Val Thr Arg Pro Glu Leu Tyr Gln Ala Ile Thr Lys Val Asn
        115                 120                 125

Tyr Val Tyr Lys Ser Gly Gln Thr Ala Pro Arg Asn Ala Pro Val Ala
    130                 135                 140

Tyr Ile Glu Leu Ser Pro Asn Asn Ser Tyr Val Gln Thr Leu Leu Asn
145                 150                 155                 160

Asp Ser His Met Lys Arg Thr Ser Ser Tyr Glu Leu Val Gly Ser Ser
                165                 170                 175

Ile Ala Arg Arg Gly Ile Glu Thr Lys Trp Ser Lys Ser His Thr Ser
            180                 185                 190

Gly Val Ser Asp Thr Asp Ser Trp Ser Leu Ala Val Ser Ala Gly Ile
        195                 200                 205

Asp Ile Glu Trp Asp Val Gly Ile Pro Leu Thr Ala Ser Ala Lys Glu
    210                 215                 220

Lys Leu Ser Leu Ser Ile Thr Gly Thr Tyr Gly Gln Ser Thr Thr Val
225                 230                 235                 240

Ser Ser Gln Asp Thr Ile Thr Gln Glu Tyr Thr Phe Ala Lys Pro Gly
                245                 250                 255

Lys Asp Tyr Lys Tyr Asp Asp Tyr Ala Tyr Ala Val Tyr Gln Leu Lys
            260                 265                 270

Ser Asn Tyr Gln Phe Ile Ala Gly Asp Ala Phe Asn Asn Leu Ile Asn
        275                 280                 285

Ser Leu Ser Phe Gly Asn Gln Phe Ser Val His Gly Asp Ala Ser Tyr
    290                 295                 300

Gln Tyr Ser Thr Asp Thr Ile Phe Ser Thr Gln Thr Pro Asp Pro Thr
305                 310                 315                 320

Pro Thr Asn Glu Lys Ser Leu Ile Gln Val Asn Phe Asn Pro Arg Phe
                325                 330                 335

Ser
```

<210> SEQ ID NO 11

-continued

<211> LENGTH: 322
<212> TYPE: PRT
<213> ORGANISM: Artificial sequence
<220> FEATURE:
<223> OTHER INFORMATION: Truncated protein

<400> SEQUENCE: 11

Met Asp Gln Gln Tyr Asp Leu Ile Ser Pro Thr Gln Asp Trp Tyr Gln
1 5 10 15

Phe Lys Thr Leu Tyr Pro Ile Ser Lys Asn Gly Val Ile Ile Ser Ser
20 25 30

Asn Leu Asp Asp Ser Ser Asn Val Leu Val Pro Glu Leu Ser Glu Asn
35 40 45

Pro Tyr Asp Pro Ile Pro Gln Ser Gly Lys Ser Thr Ile Gln Thr Ala
50 55 60

Val Arg Ser Pro Glu Ala Leu Tyr Ile Ile Leu Thr Thr Asn Asn Ser
65 70 75 80

Leu Ser Phe Gly Gly Gly Thr Asn Thr Met Ile Ala Thr Arg Ile Ala
85 90 95

Leu Leu Ser Val Thr Arg Pro Glu Leu Tyr Gln Ala Ile Thr Lys Val
100 105 110

Asn Tyr Val Tyr Lys Ser Gly Gln Thr Ala Pro Arg Asn Ala Pro Val
115 120 125

Ala Tyr Ile Glu Leu Ser Pro Asn Asn Ser Tyr Val Gln Thr Leu Leu
130 135 140

Asn Asp Ser His Met Lys Arg Thr Ser Ser Tyr Glu Leu Val Gly Ser
145 150 155 160

Ser Ile Ala Arg Arg Gly Ile Glu Thr Lys Trp Ser Lys Ser His Thr
165 170 175

Ser Gly Val Ser Asp Thr Asp Ser Trp Ser Leu Ala Val Ser Ala Gly
180 185 190

Ile Asp Ile Glu Trp Asp Val Gly Ile Pro Leu Thr Ala Ser Ala Lys
195 200 205

Glu Lys Leu Ser Leu Ser Ile Thr Gly Thr Tyr Gly Gln Ser Thr Thr
210 215 220

Val Ser Ser Gln Asp Thr Ile Thr Gln Glu Tyr Thr Phe Ala Lys Pro
225 230 235 240

Gly Lys Asp Tyr Lys Tyr Asp Asp Tyr Ala Tyr Ala Val Tyr Gln Leu
245 250 255

Lys Ser Asn Tyr Gln Phe Ile Ala Gly Asp Ala Phe Asn Asn Leu Ile
260 265 270

Asn Ser Leu Ser Phe Gly Asn Gln Phe Ser Val His Gly Asp Ala Ser
275 280 285

Tyr Gln Tyr Ser Thr Asp Thr Ile Phe Ser Thr Gln Thr Pro Asp Pro
290 295 300

Thr Pro Thr Asn Glu Lys Ser Leu Ile Gln Val Asn Phe Asn Pro Arg
305 310 315 320

Phe Ser

<210> SEQ ID NO 12
<211> LENGTH: 311
<212> TYPE: PRT
<213> ORGANISM: Artificial sequence
<220> FEATURE:
<223> OTHER INFORMATION: Truncated protein

<400> SEQUENCE: 12

-continued

Met Asp Trp Tyr Gln Phe Lys Thr Leu Tyr Pro Ile Ser Lys Asn Gly
1               5                   10                  15

Val Ile Ile Ser Ser Asn Leu Asp Asp Ser Ser Asn Val Leu Val Pro
            20                  25                  30

Glu Leu Ser Glu Asn Pro Tyr Asp Pro Ile Pro Gln Ser Gly Lys Ser
        35                  40                  45

Thr Ile Gln Thr Ala Val Arg Ser Pro Glu Ala Leu Tyr Ile Ile Leu
    50                  55                  60

Thr Thr Asn Asn Ser Leu Ser Phe Gly Gly Gly Thr Asn Thr Met Ile
65                  70                  75                  80

Ala Thr Arg Ile Ala Leu Leu Ser Val Thr Arg Pro Glu Leu Tyr Gln
                85                  90                  95

Ala Ile Thr Lys Val Asn Tyr Val Tyr Lys Ser Gly Gln Thr Ala Pro
            100                 105                 110

Arg Asn Ala Pro Val Ala Tyr Ile Glu Leu Ser Pro Asn Asn Ser Tyr
        115                 120                 125

Val Gln Thr Leu Leu Asn Asp Ser His Met Lys Arg Thr Ser Ser Tyr
    130                 135                 140

Glu Leu Val Gly Ser Ser Ile Ala Arg Arg Gly Ile Glu Thr Lys Trp
145                 150                 155                 160

Ser Lys Ser His Thr Ser Gly Val Ser Asp Thr Asp Ser Trp Ser Leu
                165                 170                 175

Ala Val Ser Ala Gly Ile Asp Ile Glu Trp Asp Val Gly Ile Pro Leu
            180                 185                 190

Thr Ala Ser Ala Lys Glu Lys Leu Ser Leu Ser Ile Thr Gly Thr Tyr
        195                 200                 205

Gly Gln Ser Thr Thr Val Ser Ser Gln Asp Thr Ile Thr Gln Glu Tyr
    210                 215                 220

Thr Phe Ala Lys Pro Gly Lys Asp Tyr Lys Tyr Asp Asp Tyr Ala Tyr
225                 230                 235                 240

Ala Val Tyr Gln Leu Lys Ser Asn Tyr Gln Phe Ile Ala Gly Asp Ala
                245                 250                 255

Phe Asn Asn Leu Ile Asn Ser Leu Ser Phe Gly Asn Gln Phe Ser Val
            260                 265                 270

His Gly Asp Ala Ser Tyr Gln Tyr Ser Thr Asp Thr Ile Phe Ser Thr
        275                 280                 285

Gln Thr Pro Asp Pro Thr Pro Thr Asn Glu Lys Ser Leu Ile Gln Val
    290                 295                 300

Asn Phe Asn Pro Arg Phe Ser
305                 310

<210> SEQ ID NO 13
<211> LENGTH: 289
<212> TYPE: PRT
<213> ORGANISM: Artificial sequence
<220> FEATURE:
<223> OTHER INFORMATION: Truncated protein

<400> SEQUENCE: 13

Met Asp Asp Ser Ser Asn Val Leu Val Pro Glu Leu Ser Glu Asn Pro
1               5                   10                  15

Tyr Asp Pro Ile Pro Gln Ser Gly Lys Ser Thr Ile Gln Thr Ala Val
            20                  25                  30

Arg Ser Pro Glu Ala Leu Tyr Ile Ile Leu Thr Thr Asn Asn Ser Leu
        35                  40                  45

-continued

```
Ser Phe Gly Gly Gly Thr Asn Thr Met Ile Ala Thr Arg Ile Ala Leu
    50                  55                  60

Leu Ser Val Thr Arg Pro Glu Leu Tyr Gln Ala Ile Thr Lys Val Asn
65                  70                  75                  80

Tyr Val Tyr Lys Ser Gly Gln Thr Ala Pro Arg Asn Ala Pro Val Ala
                85                  90                  95

Tyr Ile Glu Leu Ser Pro Asn Asn Ser Tyr Val Gln Thr Leu Leu Asn
            100                 105                 110

Asp Ser His Met Lys Arg Thr Ser Ser Tyr Glu Leu Val Gly Ser Ser
        115                 120                 125

Ile Ala Arg Arg Gly Ile Glu Thr Lys Trp Ser Lys Ser His Thr Ser
    130                 135                 140

Gly Val Ser Asp Thr Asp Ser Trp Ser Leu Ala Val Ser Ala Gly Ile
145                 150                 155                 160

Asp Ile Glu Trp Asp Val Gly Ile Pro Leu Thr Ala Ser Ala Lys Glu
                165                 170                 175

Lys Leu Ser Leu Ser Ile Thr Gly Thr Tyr Gly Gln Ser Thr Thr Val
            180                 185                 190

Ser Ser Gln Asp Thr Ile Thr Gln Glu Tyr Thr Phe Ala Lys Pro Gly
        195                 200                 205

Lys Asp Tyr Lys Tyr Asp Asp Tyr Ala Tyr Ala Val Tyr Gln Leu Lys
    210                 215                 220

Ser Asn Tyr Gln Phe Ile Ala Gly Asp Ala Phe Asn Asn Leu Ile Asn
225                 230                 235                 240

Ser Leu Ser Phe Gly Asn Gln Phe Ser Val His Gly Asp Ala Ser Tyr
                245                 250                 255

Gln Tyr Ser Thr Asp Thr Ile Phe Ser Thr Gln Thr Pro Asp Pro Thr
            260                 265                 270

Pro Thr Asn Glu Lys Ser Leu Ile Gln Val Asn Phe Asn Pro Arg Phe
        275                 280                 285

Ser


<210> SEQ ID NO 14
<211> LENGTH: 269
<212> TYPE: PRT
<213> ORGANISM: Artificial sequence
<220> FEATURE:
<223> OTHER INFORMATION: Truncated protein

<400> SEQUENCE: 14

Met Asn Lys Lys Ser Ile Thr His Glu Glu Phe Ile Arg Gln Leu Lys
1               5                   10                  15

Glu Tyr Asn Leu Asp Asn Asn Leu Asn Tyr His Asp Pro Ala Val Leu
            20                  25                  30

Lys Lys Ile Asn Glu Leu Leu Pro Ala Asp Gln Gln Tyr Asp Leu Ile
        35                  40                  45

Ser Pro Thr Gln Asp Trp Tyr Gln Phe Lys Thr Leu Tyr Pro Ile Ser
    50                  55                  60

Lys Asn Gly Val Ile Ile Ser Ser Asn Leu Asp Asp Ser Ser Asn Val
65                  70                  75                  80

Leu Val Pro Glu Leu Ser Glu Asn Pro Tyr Asp Pro Ile Pro Gln Ser
                85                  90                  95

Gly Lys Ser Thr Ile Gln Thr Ala Val Arg Ser Pro Glu Ala Leu Tyr
            100                 105                 110
```

-continued

```
Ile Ile Leu Thr Thr Asn Asn Ser Leu Ser Phe Gly Gly Gly Thr Asn
        115                 120                 125

Thr Met Ile Ala Thr Arg Ile Ala Leu Leu Ser Val Thr Arg Pro Glu
    130                 135                 140

Leu Tyr Gln Ala Ile Thr Lys Val Asn Tyr Val Tyr Lys Ser Gly Gln
145                 150                 155                 160

Thr Ala Pro Arg Asn Ala Pro Val Ala Tyr Ile Glu Leu Ser Pro Asn
                165                 170                 175

Asn Ser Tyr Val Gln Thr Leu Leu Asn Asp Ser His Met Lys Arg Thr
            180                 185                 190

Ser Ser Tyr Glu Leu Val Gly Ser Ser Ile Ala Arg Arg Gly Ile Glu
        195                 200                 205

Thr Lys Trp Ser Lys Ser His Thr Ser Gly Val Ser Asp Thr Asp Ser
    210                 215                 220

Trp Ser Leu Ala Val Ser Ala Gly Ile Asp Ile Glu Trp Asp Val Gly
225                 230                 235                 240

Ile Pro Leu Thr Ala Ser Ala Lys Glu Lys Leu Ser Leu Ser Ile Thr
                245                 250                 255

Gly Thr Tyr Gly Gln Ser Thr Thr Val Ser Ser Gln Asp
            260                 265


<210> SEQ ID NO 15
<211> LENGTH: 280
<212> TYPE: PRT
<213> ORGANISM: Artificial sequence
<220> FEATURE:
<223> OTHER INFORMATION: Truncated protein

<400> SEQUENCE: 15

Met Asn Lys Lys Ser Ile Thr His Glu Glu Phe Ile Arg Gln Leu Lys
1               5                   10                  15

Glu Tyr Asn Leu Asp Asn Asn Leu Asn Tyr His Asp Pro Ala Val Leu
            20                  25                  30

Lys Lys Ile Asn Glu Leu Leu Pro Ala Asp Gln Gln Tyr Asp Leu Ile
        35                  40                  45

Ser Pro Thr Gln Asp Trp Tyr Gln Phe Lys Thr Leu Tyr Pro Ile Ser
    50                  55                  60

Lys Asn Gly Val Ile Ile Ser Ser Asn Leu Asp Asp Ser Ser Asn Val
65                  70                  75                  80

Leu Val Pro Glu Leu Ser Glu Asn Pro Tyr Asp Pro Ile Pro Gln Ser
                85                  90                  95

Gly Lys Ser Thr Ile Gln Thr Ala Val Arg Ser Pro Glu Ala Leu Tyr
            100                 105                 110

Ile Ile Leu Thr Thr Asn Asn Ser Leu Ser Phe Gly Gly Gly Thr Asn
        115                 120                 125

Thr Met Ile Ala Thr Arg Ile Ala Leu Leu Ser Val Thr Arg Pro Glu
    130                 135                 140

Leu Tyr Gln Ala Ile Thr Lys Val Asn Tyr Val Tyr Lys Ser Gly Gln
145                 150                 155                 160

Thr Ala Pro Arg Asn Ala Pro Val Ala Tyr Ile Glu Leu Ser Pro Asn
                165                 170                 175

Asn Ser Tyr Val Gln Thr Leu Leu Asn Asp Ser His Met Lys Arg Thr
            180                 185                 190

Ser Ser Tyr Glu Leu Val Gly Ser Ser Ile Ala Arg Arg Gly Ile Glu
        195                 200                 205
```

-continued

```
Thr Lys Trp Ser Lys Ser His Thr Ser Gly Val Ser Asp Thr Asp Ser
    210                 215                 220

Trp Ser Leu Ala Val Ser Ala Gly Ile Asp Ile Glu Trp Asp Val Gly
225                 230                 235                 240

Ile Pro Leu Thr Ala Ser Ala Lys Glu Lys Leu Ser Leu Ser Ile Thr
                245                 250                 255

Gly Thr Tyr Gly Gln Ser Thr Thr Val Ser Ser Gln Asp Thr Ile Thr
            260                 265                 270

Gln Glu Tyr Thr Phe Ala Lys Pro
        275                 280


<210> SEQ ID NO 16
<211> LENGTH: 288
<212> TYPE: PRT
<213> ORGANISM: Artificial sequence
<220> FEATURE:
<223> OTHER INFORMATION: Truncated protein

<400> SEQUENCE: 16

Met Asn Lys Lys Ser Ile Thr His Glu Glu Phe Ile Arg Gln Leu Lys
1               5                   10                  15

Glu Tyr Asn Leu Asp Asn Asn Leu Asn Tyr His Asp Pro Ala Val Leu
            20                  25                  30

Lys Lys Ile Asn Glu Leu Leu Pro Ala Asp Gln Gln Tyr Asp Leu Ile
        35                  40                  45

Ser Pro Thr Gln Asp Trp Tyr Gln Phe Lys Thr Leu Tyr Pro Ile Ser
    50                  55                  60

Lys Asn Gly Val Ile Ile Ser Ser Asn Leu Asp Asp Ser Ser Asn Val
65                  70                  75                  80

Leu Val Pro Glu Leu Ser Glu Asn Pro Tyr Asp Pro Ile Pro Gln Ser
                85                  90                  95

Gly Lys Ser Thr Ile Gln Thr Ala Val Arg Ser Pro Glu Ala Leu Tyr
            100                 105                 110

Ile Ile Leu Thr Thr Asn Asn Ser Leu Ser Phe Gly Gly Gly Thr Asn
        115                 120                 125

Thr Met Ile Ala Thr Arg Ile Ala Leu Leu Ser Val Thr Arg Pro Glu
    130                 135                 140

Leu Tyr Gln Ala Ile Thr Lys Val Asn Tyr Val Tyr Lys Ser Gly Gln
145                 150                 155                 160

Thr Ala Pro Arg Asn Ala Pro Val Ala Tyr Ile Glu Leu Ser Pro Asn
                165                 170                 175

Asn Ser Tyr Val Gln Thr Leu Leu Asn Asp Ser His Met Lys Arg Thr
            180                 185                 190

Ser Ser Tyr Glu Leu Val Gly Ser Ser Ile Ala Arg Arg Gly Ile Glu
        195                 200                 205

Thr Lys Trp Ser Lys Ser His Thr Ser Gly Val Ser Asp Thr Asp Ser
    210                 215                 220

Trp Ser Leu Ala Val Ser Ala Gly Ile Asp Ile Glu Trp Asp Val Gly
225                 230                 235                 240

Ile Pro Leu Thr Ala Ser Ala Lys Glu Lys Leu Ser Leu Ser Ile Thr
                245                 250                 255

Gly Thr Tyr Gly Gln Ser Thr Thr Val Ser Ser Gln Asp Thr Ile Thr
            260                 265                 270

Gln Glu Tyr Thr Phe Ala Lys Pro Gly Lys Asp Tyr Lys Tyr Asp Asp
        275                 280                 285
```

-continued

<210> SEQ ID NO 17
<211> LENGTH: 332
<212> TYPE: PRT
<213> ORGANISM: Artificial sequence
<220> FEATURE:
<223> OTHER INFORMATION: Truncated protein

<400> SEQUENCE: 17

```
Met Asn Lys Lys Ser Ile Thr His Glu Glu Phe Ile Arg Gln Leu Lys
1               5                   10                  15

Glu Tyr Asn Leu Asp Asn Asn Leu Asn Tyr His Asp Pro Ala Val Leu
            20                  25                  30

Lys Lys Ile Asn Glu Leu Leu Pro Ala Asp Gln Gln Tyr Asp Leu Ile
        35                  40                  45

Ser Pro Thr Gln Asp Trp Tyr Gln Phe Lys Thr Leu Tyr Pro Ile Ser
    50                  55                  60

Lys Asn Gly Val Ile Ile Ser Ser Asn Leu Asp Asp Ser Ser Asn Val
65                  70                  75                  80

Leu Val Pro Glu Leu Ser Glu Asn Pro Tyr Asp Pro Ile Pro Gln Ser
                85                  90                  95

Gly Lys Ser Thr Ile Gln Thr Ala Val Arg Ser Pro Glu Ala Leu Tyr
            100                 105                 110

Ile Ile Leu Thr Thr Asn Asn Ser Leu Ser Phe Gly Gly Gly Thr Asn
        115                 120                 125

Thr Met Ile Ala Thr Arg Ile Ala Leu Leu Ser Val Thr Arg Pro Glu
    130                 135                 140

Leu Tyr Gln Ala Ile Thr Lys Val Asn Tyr Val Tyr Lys Ser Gly Gln
145                 150                 155                 160

Thr Ala Pro Arg Asn Ala Pro Val Ala Tyr Ile Glu Leu Ser Pro Asn
                165                 170                 175

Asn Ser Tyr Val Gln Thr Leu Leu Asn Asp Ser His Met Lys Arg Thr
            180                 185                 190

Ser Ser Tyr Glu Leu Val Gly Ser Ser Ile Ala Arg Arg Gly Ile Glu
        195                 200                 205

Thr Lys Trp Ser Lys Ser His Thr Ser Gly Val Ser Asp Thr Asp Ser
    210                 215                 220

Trp Ser Leu Ala Val Ser Ala Gly Ile Asp Ile Glu Trp Asp Val Gly
225                 230                 235                 240

Ile Pro Leu Thr Ala Ser Ala Lys Glu Lys Leu Ser Leu Ser Ile Thr
                245                 250                 255

Gly Thr Tyr Gly Gln Ser Thr Thr Val Ser Ser Gln Asp Thr Ile Thr
            260                 265                 270

Gln Glu Tyr Thr Phe Ala Lys Pro Gly Lys Asp Tyr Lys Tyr Asp Asp
        275                 280                 285

Tyr Ala Tyr Ala Val Tyr Gln Leu Lys Ser Asn Tyr Gln Phe Ile Ala
    290                 295                 300

Gly Asp Ala Phe Asn Asn Leu Ile Asn Ser Leu Ser Phe Gly Asn Gln
305                 310                 315                 320

Phe Ser Val His Gly Asp Ala Ser Tyr Gln Tyr Ser
                325                 330
```

<210> SEQ ID NO 18
<211> LENGTH: 342
<212> TYPE: PRT
<213> ORGANISM: Artificial sequence
<220> FEATURE:

-continued

<223> OTHER INFORMATION: Truncated protein

<400> SEQUENCE: 18

```
Met Asn Lys Lys Ser Ile Thr His Glu Glu Phe Ile Arg Gln Leu Lys
1               5                   10                  15

Glu Tyr Asn Leu Asp Asn Asn Leu Asn Tyr His Asp Pro Ala Val Leu
            20                  25                  30

Lys Lys Ile Asn Glu Leu Leu Pro Ala Asp Gln Gln Tyr Asp Leu Ile
        35                  40                  45

Ser Pro Thr Gln Asp Trp Tyr Gln Phe Lys Thr Leu Tyr Pro Ile Ser
    50                  55                  60

Lys Asn Gly Val Ile Ile Ser Ser Asn Leu Asp Asp Ser Ser Asn Val
65                  70                  75                  80

Leu Val Pro Glu Leu Ser Glu Asn Pro Tyr Asp Pro Ile Pro Gln Ser
                85                  90                  95

Gly Lys Ser Thr Ile Gln Thr Ala Val Arg Ser Pro Glu Ala Leu Tyr
            100                 105                 110

Ile Ile Leu Thr Thr Asn Asn Ser Leu Ser Phe Gly Gly Gly Thr Asn
        115                 120                 125

Thr Met Ile Ala Thr Arg Ile Ala Leu Leu Ser Val Thr Arg Pro Glu
    130                 135                 140

Leu Tyr Gln Ala Ile Thr Lys Val Asn Tyr Val Tyr Lys Ser Gly Gln
145                 150                 155                 160

Thr Ala Pro Arg Asn Ala Pro Val Ala Tyr Ile Glu Leu Ser Pro Asn
                165                 170                 175

Asn Ser Tyr Val Gln Thr Leu Leu Asn Asp Ser His Met Lys Arg Thr
            180                 185                 190

Ser Ser Tyr Glu Leu Val Gly Ser Ser Ile Ala Arg Arg Gly Ile Glu
        195                 200                 205

Thr Lys Trp Ser Lys Ser His Thr Ser Gly Val Ser Asp Thr Asp Ser
    210                 215                 220

Trp Ser Leu Ala Val Ser Ala Gly Ile Asp Ile Glu Trp Asp Val Gly
225                 230                 235                 240

Ile Pro Leu Thr Ala Ser Ala Lys Glu Lys Leu Ser Leu Ser Ile Thr
                245                 250                 255

Gly Thr Tyr Gly Gln Ser Thr Thr Val Ser Ser Gln Asp Thr Ile Thr
            260                 265                 270

Gln Glu Tyr Thr Phe Ala Lys Pro Gly Lys Asp Tyr Lys Tyr Asp Asp
        275                 280                 285

Tyr Ala Tyr Ala Val Tyr Gln Leu Lys Ser Asn Tyr Gln Phe Ile Ala
    290                 295                 300

Gly Asp Ala Phe Asn Asn Leu Ile Asn Ser Leu Ser Phe Gly Asn Gln
305                 310                 315                 320

Phe Ser Val His Gly Asp Ala Ser Tyr Gln Tyr Ser Thr Asp Thr Ile
                325                 330                 335

Phe Ser Thr Gln Thr Pro
            340
```

<210> SEQ ID NO 19
<211> LENGTH: 359
<212> TYPE: PRT
<213> ORGANISM: Artificial sequence
<220> FEATURE:
<223> OTHER INFORMATION: Truncated protein

<400> SEQUENCE: 19

-continued

```
Met Asn Lys Lys Ser Ile Thr His Glu Glu Phe Ile Arg Gln Leu Lys
1               5                   10                  15

Glu Tyr Asn Leu Asp Asn Asn Leu Asn Tyr His Asp Pro Ala Val Leu
            20                  25                  30

Lys Lys Ile Asn Glu Leu Leu Pro Ala Asp Gln Gln Tyr Asp Leu Ile
        35                  40                  45

Ser Pro Thr Gln Asp Trp Tyr Gln Phe Lys Thr Leu Tyr Pro Ile Ser
    50                  55                  60

Lys Asn Gly Val Ile Ile Ser Ser Asn Leu Asp Asp Ser Ser Asn Val
65                  70                  75                  80

Leu Val Pro Glu Leu Ser Glu Asn Pro Tyr Asp Pro Ile Pro Gln Ser
                85                  90                  95

Gly Lys Ser Thr Ile Gln Thr Ala Val Arg Ser Pro Glu Ala Leu Tyr
            100                 105                 110

Ile Ile Leu Thr Thr Asn Asn Ser Leu Ser Phe Gly Gly Gly Thr Asn
        115                 120                 125

Thr Met Ile Ala Thr Arg Ile Ala Leu Leu Ser Val Thr Arg Pro Glu
    130                 135                 140

Leu Tyr Gln Ala Ile Thr Lys Val Asn Tyr Val Tyr Lys Ser Gly Gln
145                 150                 155                 160

Thr Ala Pro Arg Asn Ala Pro Val Ala Tyr Ile Glu Leu Ser Pro Asn
                165                 170                 175

Asn Ser Tyr Val Gln Thr Leu Leu Asn Asp Ser His Met Lys Arg Thr
            180                 185                 190

Ser Ser Tyr Glu Leu Val Gly Ser Ser Ile Ala Arg Arg Gly Ile Glu
        195                 200                 205

Thr Lys Trp Ser Lys Ser His Thr Ser Gly Val Ser Asp Thr Asp Ser
    210                 215                 220

Trp Ser Leu Ala Val Ser Ala Gly Ile Asp Ile Glu Trp Asp Val Gly
225                 230                 235                 240

Ile Pro Leu Thr Ala Ser Ala Lys Glu Lys Leu Ser Leu Ser Ile Thr
                245                 250                 255

Gly Thr Tyr Gly Gln Ser Thr Thr Val Ser Ser Gln Asp Thr Ile Thr
            260                 265                 270

Gln Glu Tyr Thr Phe Ala Lys Pro Gly Lys Asp Tyr Lys Tyr Asp Asp
        275                 280                 285

Tyr Ala Tyr Ala Val Tyr Gln Leu Lys Ser Asn Tyr Gln Phe Ile Ala
    290                 295                 300

Gly Asp Ala Phe Asn Asn Leu Ile Asn Ser Leu Ser Phe Gly Asn Gln
305                 310                 315                 320

Phe Ser Val His Gly Asp Ala Ser Tyr Gln Tyr Ser Thr Asp Thr Ile
                325                 330                 335

Phe Ser Thr Gln Thr Pro Asp Pro Thr Pro Thr Asn Glu Lys Ser Leu
            340                 345                 350

Ile Gln Val Asn Phe Asn Pro
        355
```

*BACILLUS THURINGIENSIS* TOXINS AND GENES FOR CONTROLLING COLEOPTERAN PESTS

CROSS-REFERENCE TO A RELATED APPLICATION

This application is a divisional of application Ser. No. 09/307,925, filed May 10, 1999 now U.S. Pat. No. 6,344, 553, which is a continuation-in-part of application Ser. No. 09/076,193, filed May 12, 1999 now U.S. Pat. No. 5,973, 231.

BACKGROUND OF THE INVENTION

Insects and other pests cost farmers billions of dollars annually in crop losses and in the expense of keeping these pests under control. The losses caused by pests in agricultural production environments include decrease in crop yield, reduced crop quality, and increased harvesting costs.

Insects of the Order Coleoptera (coleopterans) are an important group of agricultural pests which cause extensive damage to crops each year. There are a number of beetles that cause significant economic damage; examples include Chrysomelid beetles (such as flea beetles and corn rootworms) and Curculionids (such as alfalfa weevils).

Flea beetles include a large number of genera (e.g., Altica, Apphthona, Argopistes, Disonycha, Epitrix, Longitarsus, Prodagricomela, Systena, Psylliodes, and Phyllotreta). *Phyllotreta striolata* includes the striped flea beetle. *Phyllotreta cruciferae* includes the canola flea beetle, the rape flea beetle, and the crucifer flea beetle. Canola, also known as rape, is an oil seed brassica (e.g., *Brassica campestris, Brassica rapa, Brassica napus*, and *Brassica juncea*).

Flea beetles include a large number of beetles that feed on the leaves of a number of grasses, cereals, and herbs. *Phyllotreta cruciferae, Phyllotreta striolata*, and *Phyllotreta undulata*, are particularly destructive annual pests that attack the leaves, stems, pods, and root tissues of susceptible plants. *Psylliodes chrysocephala*, a flea beetle, is also a destructive, biennial pest that attacks the stems and leaves of susceptible plants.

Chemical pesticides have provided effective pest control; however, the public has become concerned about contamination of food with residual chemicals and of the environment, including soil, surface water, and ground water. Working with pesticides may also pose hazards to the persons applying them. Stringent new restrictions on the use of pesticides and the elimination of some effective pesticides from the marketplace could limit economical and effective options for controlling costly pests.

In addition, the regular use of pesticides for the control of unwanted organisms can select for resistant strains. This has occurred in many species of economically important insects and other pests. The development of pesticide resistance necessitates a continuing search for new control agents having different modes of action.

Thus, there is an urgent need to identify new methods and compositions for controlling pests, such as the many different types of coleopterans that cause considerable damage to susceptible plants.

Certain strains of the soil microbe *Bacillus thuringiensis* (*B.t.*), a Gram-positive, spore-forming bacterium, can be characterized by parasporal crystalline protein inclusions. These inclusions often appear microscopically as distinctively shaped crystals. The proteins can be highly toxic to pests and are specific in their toxic activity. These δ-endotoxins, which are produced by certain *B.t.* strains, are synthesized by sporulating cells. Certain types of *B.t.* toxins, upon being ingested by a susceptible insect, are transformed into biologically active moieties by the insect gut juice proteases. The primary target is cells of the insect gut epithelium, which are rapidly destroyed by the toxin.

Certain Bacillus toxin genes have been isolated and sequenced. The cloning and expression of a *B.t.* crystal protein gene in *Escherichia coli* has been described in the published literature. In addition, with the use of genetic engineering techniques, new approaches for delivering these Bacillus toxins to agricultural environments are under development, including the use of plants genetically engineered with toxin genes for insect resistance and the use of stabilized intact microbial cells as *B.t.* endotoxin delivery vehicles. Recombinant DNA-based *B.t.* products have been produced and approved for use. Thus, isolated Bacillus toxin genes are becoming commercially valuable.

Until fairly recently, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, new subspecies of *B.t.* have been identified, and investigators have discovered *B.t.* pesticides with specificities for a much broader range of pests. For example, other species of *B.t.,* namely *israelensis* and *morrisoni* (a.k.a. *tenebrionis,* a.k.a. *B.t. M*-7, a.k.a. *B.t. san diego*), have been used commercially to control insects of the orders Diptera and Coleoptera, respectively.

Höfte and Whiteley (Höfte, H., H. R. Whiteley [1989] *Microbiological Reviews* 52(2):242–255) classified *B.t.* crystal protein genes into four major classes. The classes were CryI (Lepidoptera-specific), CryII (Lepidoptera- and Diptera-specific), CryIII (Coleoptera-specific), and CryIV (Diptera-specific). CryV and CryVI were proposed to designate a class of toxin genes that are nematode-specific. Other classes of *B.t.* genes have now been identified.

The 1989 nomenclature and classification scheme of Höfte and Whiteley for crystal proteins was based on both the deduced amino acid sequence and the host range of the toxin. That system was adapted to cover 14 different types of toxin genes which were divided into five major classes. As more toxin genes were discovered, that system started to become unworkable, as genes with similar sequences were found to have significantly different insecticidal specificities. A revised nomenclature scheme has been proposed which is based solely on amino acid identity (Crickmore et al. [1996] Society for Invertebrate Pathology, 29th Annual Meeting, 3rd International Colloquium on *Bacillus thuringiensis,* University of Cordoba, Cordoba, Spain, September 1–6, abstract). The mnemonic "cry" has been retained for all of the toxin genes except cytA and cytB, which remain a separate class. Roman numerals have been exchanged for Arabic numerals in the primary rank, and the parentheses in the tertiary rank have been removed. Many of the original names have been retained, with the noted exceptions, although a number have been reclassified. See also "Revisions of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean, *Microbiology and Molecular Biology Reviews* (1998) Vol. 62:807–813; and Crickmore, Zeigler, Feitelson, Schnepf, Van Rie, Lereclus, Baum, and Dean, "*Bacillus thuringiensis* toxin nomenclature" (1999) http://www.biols.susx.ac.uk/Home/Neil_Crickmore/Bt/index.html. That system uses the freely available software applications CLUSTAL W and PHYLIP. The NEIGHBOR application within the PHYLIP package uses an arithmetic averages (UPGMA) algorithm.

*B.t.* isolate PS86A1 is disclosed in the following U.S. Pat. No. 4,849,217 (activity against alfalfa weevil); U.S. Pat. No. 5,208,017 (activity against corn rootworm); U.S. Pat. No. 5,286,485 (activity against lepidopterans); and U.S. Pat. No. 5,427,786 (activity against Phyllotreta genera). A gene from PS86A1 was cloned into *B.t.* MR506, which is disclosed in U.S. Pat. No. 5,670,365 (activity against nematodes) and PCT international patent application publication no. WO93/04587 (activity against lepidopterans). The sequences of a gene and a Cry6A (CryVIA) toxin from PS86A1 are disclosed in the following U.S. Pat. No. 5,186,934 (activity against Hypera genera); U.S. Pat. No. 5,273,746 (lice); U.S. Pat. Nos. 5,262,158 and 5,424,410 (activity against mites); as well as in PCT international patent application publication no. WO94/23036 (activity against wireworms). U.S. Pat. Nos. 5,262,159 and 5,468,636, disclose PS86A1, the sequence of a gene and toxin therefrom, and a generic formula for toxins having activity against aphids.

*B.t.* isolate PS52A1 is disclosed by the following U.S. patents as being active against nematodes: U.S. Pat. Nos. 4,861,595, 4,948,734, 5,093,120, 5,262,399, 5,236,843, 5,322,932, and 5,670,365. PS52A1 is also disclosed in U.S. Pat. No. 4,849,217, supra, and PCT international patent application publication no. WO95/02694 (activity against Calliphoridae). The sequences of a gene and a nematode-active toxin from PS52A1 are disclosed in U.S. Pat. No. 5,439,881 and European patent application publication no. EP 0462721. PS52A1, the sequence of a gene and nematode-active toxin therefrom, and a generic formula for CryVIA toxins are disclosed in PCT international patent application publication no. WO92/19739.

As a result of extensive research, other patents have issued for new *B.t.* isolates and new uses of *B.t.* isolates. However, the discovery of new Bacillus isolates, toxins, and genes, and new uses of known *B.t.* isolates remains an empirical, unpredictable art.

Although *B.t.* strains PS86A1 and PS52A1, and a gene and toxin therefrom, were known to have certain pesticidal activity, additional genes encoding active toxins from these isolates were not previously known in the art.

BRIEF SUMMARY OF THE INVENTION

The subject invention provides novel genes encoding pesticidal toxins. Preferred, novel toxin genes of the subject invention are designated 86A1(b) and 52A1(b). These genes encode toxins that are active against plant pests, preferably insects, preferably coleopterans, and most preferably flea beetles of the genus Phyllotreta.

In a preferred embodiment, the subject invention concerns plants and plant cells transformed with at least one polynucleotide sequence of the subject invention such that the transformed plant cells express pesticidal toxins in tissues consumed by the target pests. Plants are transformed in this manner in order to confer pest resistance upon said plants. In these preferred embodiments, pests contact the toxins expressed by the transformed plant by ingesting or consuming the plant tissues expressing the toxin. Such transformation of plants can be accomplished using techniques known to those skilled in the art. Proteins expressed in this manner are better protected from environmental degradation and inactivation. There are numerous other benefits of using transformed plants of the subject invention.

In an alternative embodiment, *B.t.* isolates of the subject invention, or recombinant microbes expressing the toxins described herein, can be used to control pests. Thus, the subject invention includes substantially intact *B.t.* cells, and recombinant cells containing the expressed toxins of the invention, treated to prolong the pesticidal activity when the substantially intact cells are applied to the environment of a target pest. The treated cell acts as a protective coating for the pesticidal toxin. The toxin becomes active upon ingestion by a target insect.

Another aspect of the subject invention includes synthetic, plant-optimized *B.t.* genes that are particularly well suited for providing stable maintenance and expression in the transformed plant.

BRIEF DESCRIPTION OF THE SEQUENCES

SEQ ID NO. 1 is a forward oligonucleotide probe for 52A1(b) and 86A1(b).

SEQ ID NO. 2 is a nucleotide sequence of a gene encoding the 86A1(b) toxin.

SEQ ID NO. 3 is an amino acid sequence of the 86A1(b) toxin.

SEQ ID NO. 4 is a nucleotide sequence of a gene encoding the 52A1(b) toxin.

SEQ ID NO. 5 is an amino acid sequence of the 52A1(b) toxin.

SEQ ID NO. 6 is a nucleotide sequence of the plant-optimized MR510 gene.

SEQ ID NO. 7 is an amino acid sequence encoded by the plant-optimized MR510 gene.

SEQ ID NO. 8 is a preferred, truncated version of the full-length, native 52A1(b) toxin. In the gene encoding this toxin (and for the genes encoding all of the following amino acid sequences shown in SEQ ID NOS. 9–19), the initiator codon for methionine has been added so that the N-terminal amino acid is methionine and not leucine (leucine is the first amino acid in the native protein). This truncation and the proteins shown in SEQ ID NOS. 9–13 have N-terminal deletions from the native protein. The natural 52A1(b) end is otherwise used in these truncations. After the first amino acid, this truncated toxin begins with amino acid 10 of the native protein. That is, the first 9 amino acids of the native protein have been replaced in favor of the single amino acid methionine. The remaining (C-terminal) portion of this toxin is the same as that of the native protein. In preferred embodiments, two stop codons are used in the gene encoding this toxin as well as in the genes encoding the following truncated proteins (SEQ ID NOS. 9–19).

SEQ ID NO. 9 is another preferred, truncated version of the full-length, native 52A1(b) protein. This protein comprises methionine added to the native protein beginning at amino acid 21 of the native protein. Thus, the first 20 N-terminal amino acids of the native protein have been replaced with methionine.

SEQ ID NO. 10 is another preferred, truncated version of the full-length, native 52A1(b) protein. In this truncation, the first 26 N-terminal amino acids of the native protein have been replaced with methionine.

SEQ ID NO. 11 is another preferred, truncated version of the full-length, native 52A 1(b) protein. In this truncation, the first 41 N-terminal amino acids of the native protein have been replaced with methionine.

SEQ ID NO. 12 is another preferred, truncated version of the full-length, native 52A1(b) protein. In this truncation, the first 52 N-terminal amino acids of the native protein have been replaced with methionine.

SEQ ID NO. 13 is another preferred, truncated version of the full-length, native 52A1(b) protein. In this truncation, the first 74 N-terminal amino acids of the native protein have been replaced with methionine.

SEQ ID NO. 14 is another preferred, truncated version of the full-length, native 52A1(b) protein. In this truncation (and in the remaining truncations shown in SEQ ID NOS. 15–19), the natural beginning of the 52A1(b) protein (with the exception that leucine has been replaced with methionine) is used. Thus, these toxins (and the genes encoding them) are the result of making C-terminal deletions to the native protein. In this truncated protein, 93 amino acids are removed from the C-terminus of the native protein. Thus, this truncated protein ends with amino acid 269 of the native protein.

SEQ ID NO. 15 is another preferred, truncated version of the full-length, native 52A1(b) protein. In this truncated protein, 82 amino acids are removed from the C-terminus of the native protein. Thus, this truncated protein ends with amino acid 280 of the native protein.

SEQ ID NO. 16 is another preferred, truncated version of the full-length, native 52A1(b) protein. In this truncated protein, 74 amino acids are removed from the C-terminus of the native a protein. Thus, this truncated protein ends with amino acid 288 of the native protein.

SEQ ID NO. 17 is another preferred, truncated version of the full-length, native 52A1(b) protein. In this truncated protein, 30 amino acids are removed from the C-terminus of the native protein. Thus, this truncated protein ends with amino acid 332 of the native protein.

SEQ ID NO. 18 is another preferred, truncated version of the full-length, native 52A1(b) protein. In this truncated protein, 20 amino acids are removed from the C-terminus of the native protein. Thus, this truncated protein ends with amino acid 342 of the native protein.

SEQ ID NO. 19 is another preferred, truncated version of the full-length, native 52A1(b) protein. In this truncated protein, three amino acids are removed from the C-terminus of the native protein. Thus, this truncated protein ends with amino acid 359 of the native protein.

DETAILED DISCLOSURE OF THE INVENTION

The subject invention provides novel genes encoding pesticidal toxins. Preferred, novel toxin genes of the subject invention are designated 86A1(b) and 52A1(b). These genes encode toxins that are active against (which can be used to control, or which are toxic to, or which are lethal to) plant pests, preferably insects, preferably coleopterans, and most preferably flea beetles of the genus Phyllotreta. The use of the subject genes and toxins for controlling other pests, such as pests of the genus Psylliodes, is also contemplated.

In a preferred embodiment, the subject invention concerns plants and plant cells transformed with at least one polynucleotide sequence of the subject invention such that the transformed plant cells express pesticidal toxins in tissues consumed by the target pests. Plants are transformed in this manner in order to confer pest resistance upon said plants. In these preferred embodiments, pests contact the toxins expressed by the transformed plant by ingesting or consuming the plant tissues expressing the toxin. Such transformation of plants can be accomplished using techniques known to those skilled in the art. Proteins expressed in this manner are better protected from environmental degradation and inactivation. There are numerous other benefits of using transformed plants of the subject invention.

In an alternative embodiment, *B.t.* isolates of the subject invention, or recombinant microbes expressing the toxins described herein, can be used to control pests. Thus, the subject invention includes substantially intact *B.t.* cells, and recombinant cells containing the expressed toxins of the invention. These cells can be treated to prolong the pesticidal activity when the substantially intact cells are applied to the environment of a target pest. See, e.g., U.S. Pat. Nos. 4,695,462; 4,861,595; and 4,695,455. The treated cell acts as a protective coating for the pesticidal toxin. The toxin becomes active upon ingestion by a target insect.

Characteristics of *Bacillus thuringiensis* isolates PS86A1 and PS52A1, such as colony morphology, inclusion type, and the sizes of alkali-soluble proteins (by SDS-PAGE), have been disclosed in, for example, U.S. Pat. No. 5,427,786 and published PCT application WO 95/02694, respectively.

Isolates useful according to the subject invention are available by virtue of deposits described in various U.S. patents. Examples of such patents are discussed in more detail in the Background section, supra. The cultures disclosed in this application have been deposited in the Agricultural Research Service Patent Culture Collection (NRRL), Northern Regional Research Center, 1815 North University Street, Peoria, Ill. 61604, USA.

TABLE 1

| Culture | Repository Accession No. | Deposit date |
|---|---|---|
| *B.t.* var. *wuhanensis* PS86A1 | NRRL B-18400 | August 16, 1988 |
| *B.t.* var. *wuhanensis* PS52A1 | NRRL B-18245 | July 28, 1987 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Genes and Toxins

Certain DNA sequences of the subject invention have been specifically exemplified herein. These sequences are exemplary of the subject invention. It should be readily apparent that the subject invention includes not only the genes and sequences specifically exemplified herein but also equivalents, variants, variations, mutants, fusions, chimerics, truncations, fragments, and smaller genes that exhibit the same or similar characteristics relating to pesticidal activity and expression in plants, as compared to those specifically disclosed herein.

Fragments of the genes and toxins specifically exemplified herein which retain the pesticidal activity of the exemplified toxins are within the scope of the subject invention. Genes and toxins useful according to the subject invention include not only the full length sequences but also fragments of these sequences which retain the characteristic pesticidal activity of the toxins specifically exemplified herein.

Variant DNA sequences are within the scope of the subject invention. As used herein, "variants" and "equivalents" refer to sequences which have nucleotide (or amino acid) substitutions, deletions, additions, or insertions which do not materially affect the expression of the subject genes, and the resultant pesticidal activity of the encoded toxins, particularly in plants. As used herein, the terms "variants" or "variations" of genes refer to nucleotide sequences which encode the same toxins or which encode equivalent toxins having pesticidal activity. As used herein, the term "equivalent if toxins" refers to toxins having the same or essentially the same biological activity against the target pests as the exemplified toxins.

Genes can be modified, and variations of genes may be readily constructed, as would be known to one skilled in the art. For example, U.S. Pat. No. 5,605,793 describes methods for generating additional molecular diversity by using DNA reassembly after random fragmentation. Standard techniques are available for making point mutations. The use of site-directed mutagenesis is known in the art. Fragments of the subject genes can be made using commercially available exonucleases or endonucleases according to standard procedures. For example, enzymes such as Bal31 can be used to systematically cut off nucleotides from the ends of these genes. Useful genes may be obtained using a variety of restriction enzymes. Proteases may be used to directly obtain active fragments of these toxins.

Because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity.

It should be apparent to a person skilled in this art that, given the sequences of the genes and toxins as set forth herein, the genes and toxins of the subject invention can be obtained through several means. For example, the subject genes may be constructed synthetically by using a gene synthesizer. The subject genes and toxins can also be derived from wild-type genes and toxins from isolates deposited at a culture depository as described above. Equivalent toxins and/or genes encoding these equivalent toxins can be derived from Bacillus isolates and/or DNA libraries using the teachings provided herein.

As the skilled artisan would readily recognize, DNA can exist in a double-stranded form. In this arrangement, one strand is complementary to the other strand and vice versa. The "coding strand" is often used in the art to refer to the strand having a series of codons (a codon is three nucleotides that can be read three-at-a-time to yield a particular amino acid) that can be read as an open reading frame (ORF) to form a protein or peptide of interest. In order to express a protein in vivo, a strand of DNA is typically translated into a complementary strand of RNA which is used as the template for the protein. As DNA is replicated in a plant (for example) additional, complementary strands of DNA are produced. Thus, the subject invention includes the use of either the exemplified polynucleotides shown in the attached sequence listing or the complementary strands. RNA and PNA (peptide nucleic acids) that are functionally equivalent to the exemplified DNA are included in the subject invention. Thus, in preferred embodiments, the direct or indirect expression of the subject polynucleotide results, directly or indirectly, in the intracellular production and maintenance of the desired polypeptide or protein.

There are a number of methods for obtaining the pesticidal toxins of the instant invention. For example, antibodies to the pesticidal toxins disclosed and claimed herein can be used to identify and isolate toxins from a mixture of proteins. Specifically, antibodies may be raised to the portions of the toxins which are most constant and most distinct from other Bacillus toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins or fragments of these toxins, can readily be prepared using standard procedures in this art.

Certain toxins of the subject invention have been specifically exemplified herein; these toxins are merely exemplary of the toxins of the subject invention. It is readily apparent that the subject invention comprises variant or equivalent toxins (and nucleotide sequences coding for equivalent toxins) having the same or similar pesticidal activity of the exemplified toxin. Equivalent genes will encode toxins that have high amino acid identity or homology with the toxins coded for by the subject genes. Equivalent toxins will have amino acid homology with an exemplified toxin. This amino acid identity will typically be greater than 60%, preferably be greater than 75%, more preferably greater than 80%, more preferably greater than 90%, and can be greater than 95%. These identities are as determined using standard alignment techniques. Preferred methods of determining percent identity are discussed in Crickmore et al., supra. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

As used herein, reference to "isolated" polynucleotides and/or "purified" toxins refers to these molecules when they are not associated with the other molecules with which they would be found in nature, and would include their use in plants. Thus, reference to "isolated and purified" signifies the involvement of the "hand of man" as described herein. Chimeric toxins and genes also involve the "hand of man."

Full length *B.t.* toxins can be expressed and then converted to active, truncated forms through the addition of appropriate reagents and/or by growing the cultures under conditions which result in the truncation of the proteins through the fortuitous action of endogenous proteases. In an alternative embodiment, the full length toxin may undergo other modifications to yield the active form of the toxin. Adjustment of the solubilization of the toxin, as well as other reaction conditions, such as pH, ionic strength, or redox potential, can be used to effect the desired modification of the toxin. Truncated toxins of the subject invention can be obtained by treating the crystalline δ-endotoxin of *Bacillus thuringiensis* with a serine protease such as bovine trypsin at an alkaline pH and preferably in the absence of β-mercaptoethanol.

Chimeric and/or fusion genes and toxins (typically produced by either combining portions from more than one Bacillus toxin or gene, or by combining full-length genes and toxins, and combinations thereof) may also be utilized according to the teachings of the subject invention. The subject invention includes the use of all or part of the toxins and genes in the production of fusion proteins and fusion genes. Chimeric toxins can also be produced by combining portions of multiple toxins.

Methods have been developed for making useful chimeric toxins by combining portions of *B.t.* crystal proteins. The portions which are combined need not, themselves, be pesticidal so long as the combination of portions creates a chimeric protein which is pesticidal. This can be done using restriction enzymes, as described in, for example, European Patent 0 228 838; Ge, A. Z., N. L. Shivarova, D. H. Dean (1989) *Proc. Natl. Acad. Sci. USA* 86:4037–4041; Ge, A. Z., D. Rivers, R. Milne, D. H. Dean (1991) *J. Biol. Chem.* 266:17954–17958; Schnepf, H. E., K. Tomczak, J. P. Ortega, H. R. Whiteley (1990) *J. Biol. Chem.* 265:20923–20930; Honee, G., D. Convents, J. Van Rie, S. Jansens, M. Peferoen, B. Visser (1991) *Mol. Microbiol.* 5:2799–2806. Alternatively, recombination using cellular recombination mechanisms can be used to achieve similar results. See, for example, Caramori, T., A. M. Albertini, A. Galizzi (1991) *Gene* 98:37–44; Widner, W. R., H. R. Whiteley (1990) *J. Bacteriol.* 172:2826–2832; Bosch, D., B. Schipper, H. van der Kliej, R. A. de Maagd, W. J. Stickema (1994) *Biotechnology* 12:915–918. A number of other methods are known in the art by which such chimeric DNAs can be made. The subject invention is meant to include chimeric proteins that utilize the novel sequences identified in the subject application.

In addition, toxins of the subject invention may be used in combination with each other or with other toxins to achieve enhanced pest control. Of course, this includes the use of the subject toxins with different toxins in pest-control schemes designed to control pests that might have developed resistance against one or more toxins.

With the teachings provided herein, one skilled in the art could readily produce and use the various toxins and polynucleotide sequences described herein.

Recombinant Hosts and Other Application Methods

The toxin-encoding genes of the subject invention can be introduced into a wide variety of microbial or plant hosts. As used herein, the term "heterologous" gene refers to a gene that does not naturally occur in the host that is transformed with the gene. In preferred embodiments, expression of the toxin gene results, directly or indirectly, in the intracellular production and maintenance of the pesticide.

When transformed plants of the subject invention are ingested by the pest, the pests will ingest the toxin. The result is a control of the pest. Benefits of in planta expression of the toxin proteins include improved protection of the pesticide from environmental degradation and inactivation. In planta use also avoids the time and expense of spraying or otherwise applying organisms and/or the toxin to the plant or the site of the pest in order to contact and control the target pest.

The subject *B.t.* toxin genes can be introduced via a suitable vector into a host, preferably a plant host. There are many compatible crops of interest, such as corn, cotton, and sunflowers.

Synthetic, plant-optimized genes, as exemplified herein, are particularly well suited for providing stable maintenance and expression of the gene in the transformed plant.

In some embodiments of the subject invention, transformed microbial hosts can be used in preliminary steps for preparing precursors that will eventually be used to transform plant cells and/or plants. Microbes transformed and used in this manner are within the scope of the subject invention. Recombinant microbes may be, for example, *B.t., E. coli,* or Pseudomonas (such as *Pseudomonas fluorescens*). Transformations can be made by those skilled in the art using standard techniques. Materials necessary for these transformations are disclosed herein or are otherwise readily available to the skilled artisan.

As an alternative to using plants transformed with a gene of the subject invention, the *B.t.* isolates, or recombinant microbes expressing the toxins described herein, can be used to control pests.

The *B.t.* isolates of the invention can be cultured using standard art media and fermentation techniques. Upon completion of the fermentation cycle, the bacteria can be harvested by first separating the *B.t.* spores and crystals from the fermentation broth by means well known in the art. The recovered *B.t.* spores, crystals, and/or toxins can be formulated into wettable powders, liquid concentrates, granules, or other formulations by the addition of surfactants, dispersants, inert carriers and other components to facilitate handling and application for particular target pests. These formulation and application procedures are all well known in the art.

The subject invention also includes mutants of the above *B.t.* isolates which have substantially the same pesticidal properties as the parent *B.t.* isolates. Mutants can be made by procedures well known in the art. Ultraviolet light and nitrosoguanidine are used extensively toward this end. An asporogenous mutant can be obtained through ethylmethane sulfonate (EMS) mutagenesis of an isolate.

Suitable microbial hosts, e.g., Pseudomonas, transformed to express one or more genes of the subject invention can be applied to the situs of the pest, where the transformed host can proliferate and/or be ingested. The result is a control of the pest.

Alternatively, the microbe hosting the toxin gene can be killed and treated under conditions that prolong the activity of the toxin and stabilize the cell; the treated cell, which retains the toxic activity, then can be applied to the environment of the target pest. See, e.g., U.S. Pat. Nos. 4,695,462; 4,861,595; and 4,695,455. Thus, the invention includes the treatment of substantially intact *B.t.* cells, and/or recombinant cells containing the expressed toxins of the invention, treated to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

Synthetic, Plant-optimized Genes

Preferred synthetic *B.t.* genes according to the present invention include nucleotide sequences that have: (1) more plant preferred codons than the native *B.t.* gene, (2) a frequency of codon usage that is closer to the codon frequency of the intended plant host than the native *B.t.* gene, or (3) substantially all codons comprised of the codon that has the highest frequency in the intended plant host. While the subject invention provides specific embodiments of synthetic genes that are particularly useful in transformed plants, other genes that are functionally equivalent to the genes exemplified herein can also be used to transform hosts, preferably plant hosts. Additional guidance for the production of synthetic genes for use in plants can be found in, for example, U.S. Pat. No. 5,380,831.

Polynucleotide Probes

One method for identifying useful toxins and genes is through the use of oligonucleotide probes. These probes are detectable nucleotide sequences. Probes provide a rapid method for identifying toxin-encoding genes. The nucleotide segments which are used as probes can be synthesized using a DNA synthesizer and standard procedures.

It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed under conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes to readily detect and characterize DNA sequences of interest.

The probes may be RNA, DNA, or PNA (peptide nucleic acid). The probe will normally have at least about 10 bases, more usually at least about 17 bases, and may have up to about 100 bases or more. Longer probes can readily be utilized, and such probes can be, for example, several kilobases in length. The probe sequence is designed to be at least substantially complementary to a portion of a gene encoding a toxin of interest. The probe need not have perfect complementarity to the sequence to which it hybridizes. The probes may be labeled utilizing techniques which are well known to those skilled in this art.

One approach for the use of probes entails first identifying by Southern blot analysis of a gene bank of the Bacillus isolate all DNA segments homologous with the disclosed nucleotide sequences. Thus, it is possible, without the aid of biological analysis, to know in advance the probable activity of many new Bacillus isolates, and of the individual gene products expressed by a given Bacillus isolate. Such a probe analysis provides a rapid method for identifying potentially commercially valuable insecticidal toxin genes within the multifarious subspecies of *B.t.* The particular hybridization technique is not essential. As improvements are made in hybridization techniques, they can be readily applied.

One useful hybridization procedure typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane.

The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

In the use of the nucleotide segments as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes can be made inherently fluorescent as described in International Application No. WO 93/16094.

Various degrees of stringency of hybridization can be employed, as described below. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes,* Stockton Press, New York, N.Y., pp. 169–170.

Hybridization of immobilized DNA on Southern blots with $^{32}P$-labeled gene-specific probes can be performed by standard methods (Maniatis et al. [1982] *Molecular Cloning. A Laboratory Manual,* Cold Spring Harbor Laboratory, Cold Spring Harbor, N.Y.). In general, hybridization and subsequent washes can be carried out under low, moderate, and/or high stringency conditions that allow for detection of target sequences with homology to the exemplified toxin genes. For double-stranded DNA gene probes, hybridization can be carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology, R. Wu, L. Grossman and K. Moldave* [*eds.*]*Academic Press, New York* 100:266–285).

Tm=81.5° C.+16.6 Log[$Na^+$]0.4(%G+C)−0.61 (%formamide)−600/length of duplex in base pairs.

Washes are typically carried out as follows:

(1) Twice at room temperature for 15 minutes in 1×SSPE, 0.1% SDS (low stringency wash).

(2) Once at Tm−20° C. for 15 minutes in 0.2×SSPE, 0.1% SDS (moderate stringency wash). Other low stringency washes include 6×SSPE, 0.1% SDS at 37° C. or 2×SSPE, 0.1% SDS at Tm−20° C.

For oligonucleotide probes, hybridization can be carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes can be determined by the following formula:

Tm (°C.)=2(number T/A base pairs)+4(number G/C base pairs) (Suggs, S. V., T. Miyake, E. H. Kawashime, M. J. Johnson, K. Itakura, and R. B. Wallace [1981] *ICN-UCLA Symp. Dev. Biol. Using Purified Genes,* D. D. Brown [ed.], Academic Press, New York, 23:683–693).

Washes are typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. In addition, formamide or aqueous washes can be used. Formamide washes require a lower temperature than aqueous washes. With a labeled DNA fragment >70 or so bases in length, the following conditions (aqueous washes) can be used:

| | |
|---|---|
| Low: | 1 or 2X SSPE, room temperature |
| Low: | 1 or 2X SSPE, 42° C. |
| Moderate: | 0.2X or 1X SSPE, 65° C. |
| High: | 0.1X SSPE, 65° C. |

Duplex formation and stability depend on substantial complementarity between the two strands of a hybrid, and, as noted above, a certain degree of mismatch can be tolerated. Therefore, useful probe sequences can include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan; other methods may become known in the future. These variants can be used in the same manner as the original primer sequences so long as the variants have substantial sequence homology with the original sequence. As used herein, substantial sequence homology refers to homology which is sufficient to enable the variant probe to function in the same capacity as the original probe. Preferably, this is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

PCR Technology

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Anaheim [1985] "Enzymatic Amplification of β-Globin Genomic Sequences and Restriction Site Analysis for Diagnosis of Sickle Cell Anemia," *Science* 230:1350–1354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated. Other enzymes which can be used are known to those skilled in the art.

DNA sequences can be designed and used as primers for PCR amplification. In performing PCR amplification, a certain degree of mismatch can be tolerated between primer and template. Therefore, mutations, deletions, and insertions (especially additions of nucleotides to the 5' end) can be produced in a given primer by methods known to an ordinarily skilled artisan.

All of the references cited herein are hereby incorporated by reference.

Following are examples which illustrate procedures for practicing the invention. These examples should not be construed as limiting. All percentages are by weight and all solvent mixture proportions are by volume unless otherwise noted.

EXAMPLE 1

Culturing the *B.t.* Isolates of the Invention

A subculture of a *B.t.* isolate can be used to inoculate the following medium (a peptone, glucose, salts medium, pH 7.2):

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and crystals, obtained in the above fermentation, can be isolated by procedures well known in the art. A frequently-used procedure is to subject the harvested fermentation broth to separation techniques, e.g., centrifugation.

EXAMPLE 2

Molecular Cloning, Expression, and Sequencing of Novel Toxin Genes from *Bacillus thuringiensis* Strains PS52A1 and PS86A1

Total cellular DNA was prepared from PS52A1 and PS86A1 *Bacillus thuringiensis* (*B.t.*) cells grown at 30° C. to an optical density of 1.0 at 600 nm. Cells were pelleted by centrifugation and resuspended in protoplast buffer (20 mg/mL lysozyme in 0.3M sucrose, 25 mM Tris-Cl [pH 8.0], 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl [pH 8.0] were added to complete lysis. The cleared lysate was extracted twice with phenol:chloroform (1:1). Nucleic acids were precipitated with two volumes of ethanol and pelleted by centrifugation. The pellet was resuspended in TE buffer (10 mM Tris-Cl [pH 8.0], 1 mM EDTA) and RNase was added to a final concentration of 50 μg/mL. After incubation at 37° C. for 1 hour, the solution was extracted once each with phenol:chloroform (1:1) and TE-saturated chloroform. From the aqueous phase, DNA was precipitated by the addition of one-tenth volume 3M NaOAc and two volumes ethanol. DNA was pelleted by centrifugation, washed with 70% ethanol, dried, and resuspended in TE buffer.

Plasmid DNA was also prepared from *B.t.* strain PS86A1. The *B.t.* cells were grown at 30° C. to an optical density of 1.0 at 600 nm. Cells were pelleted by centrifugation and resuspended in protoplast buffer (20 mg/mL lysozyme in 0.3M sucrose, 25 mM Tris-Cl [pH 8.0], 25 mM EDTA). After incubation on ice for 30 minutes, ten volumes of lysis buffer (0.085 M NaOH, 0.1% SDS in TE buffer) were added. The lysate was rocked gently at room temperature for 30 minutes. One-half volume 3M KOAc was added to the suspension for incubation at 4° C. overnight. Nucleic acids were precipitated with one volume isopropanol and pelleted by centrifugation, washed with 70% ethanol, dried, and resuspended in TE buffer. The DNA suspension was further purified by extraction once with phenol:chloroform (1:1). DNA in the aqueous phase was precipitated by the addition of one-tenth volume 3M NaOAc and one volume of isopropanol. DNA was pelleted by centrifugation, washed with 70% ethanol, dried, and resuspended in TE buffer. CsCl was added at equal weight to volume of DNA solution, and ethidium bromide was added to a final concentration of 0.5 mg/mL. The plasmid DNA was separated from the extraneous nucleic acids by overnight ultracentrifugation. The recovered plasmid band was extracted five times with excess water-saturated butanol, and dialyzed against TE buffer. DNA was precipitated, pelleted, washed, dried and resuspended in TE buffer as described previously. Based on N-terminal amino acid sequencing data of the PS86A1 45 kDa polypeptide, the following "forward" oligonucleotide of sequence (SEQ ID NO. 1) was synthesized for use in Southern hybridizations:

5'-TGGATAAAAAATCWATWACACATGAA-
GAATTTATWMGACA-3' wherein W=A or T, and M=A or C, according to standard IUPAC conventions.

PS86A1 total cellular and plasmid DNA were digested with selected restriction endonucleases, electrophoresed on an agarose gel, subsequently blotted onto a nylon membrane, and immobilized by "baking" the membrane at 80° C. Restriction, fragment length polymorphism (RFLP) analysis was performed using the oligonucleotide probe described above. Southern blots were hybridized overnight in 6×SSPE, 5×Denhardt's solution, 0.1 mg/mL single stranded carrier DNA and 0.1% SDS at 37° C. The blots were then washed in 1×SSPE, 0.1% SDS at 37° C., air-dried, then exposed to X-ray film. Autoradiography identified an approximately 6.6 kbp XbaI band in both the total cellular and plasmid DNA blots that was theorized to contain all or part of the PS86B1(b) toxin gene.

The approximately 6.6 kbp XbaI fragment was cloned into pHTBlueII (an *E. coli/B. thuringiensis* shuttle vector composed of pBluescript II SK- (Stratagene, La Jolla, Calif.) and the replication origin from a resident *B.t.* plasmid (Lereclus et al. [1989] *FEMS Microbiology Letters* 60:211–218). Polymerase chain reaction (PCR) mapping to determine if the fragment contained the full-length gene was conducted using the "forward" oligonucleotide primer described previously and vector primers. The "forward" primer combined with vector primer T7 resulted in amplification of only an approximately 400 bp-sized fragment, instead of the approximately 1.0 kbp gene expected to encode a protein of 45 kDa length. This established that only approximately one-third of the PS86A1(b) toxin gene was cloned. Further verification was provided by dideoxynucleotide sequencing (Sanger et al. [1977] *Proc. Natl. Acad. Sci. USA* 74:5463–5467) using Sequenase (US Biochemical, Cleveland, Ohio) on the subgene construct. The PCR fragment was subsequently radiolabelled with $^{32}P$ and used as a probe in standard hybridizations of Southern blots and gene libraries of PS86A1 and PS52A1 total cellular DNA.

A gene library was constructed from PS86A1 total cellular DNA partially digested with Sau3A I. Partial restriction digests were fractionated by agarose gel electrophoresis.

DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The Sau3A I inserts were ligated into BamHI-digested LambdaGem-11 (Promega, Madison, Wis.). Recombinant phage were packaged and plated on *E. coli* KW251 (Promega, Madison, Wis.) cells. Plaques were screened by transfer of recombinant phage DNA to filters and hybridization with the PCR probe described previously. Hybridization was carried out overnight at 37° C. in a solution consisting of 6×SSPE, 5×Denhardt's solution, 0.1 mg/mL single stranded carrier DNA, and 0.1% SDS. The filters were subsequently washed in 1×SSPE and 0.1% SDS at 37° C., air-dried, and then exposed to X-ray film. Hybridizing phage were plaque-purified and used to infect liquid cultures of *E. coli* KW251 cells for isolation of DNA by standard procedures (Maniatis et al. [1982] *Molecular Cloning: A Laboratory Manual,* Cold Spring Harbor Laboratory, Cold Spring Harbor, N.Y.). Southern blotting of plaque-purified hybridizing phage DNA digested with selected restriction endonucleases using the PCR-amplified probe and washing conditions as described above revealed an approximately 2.3 kbp EcoR V+Sal I fragment believed to contain the PS86A1(b) gene.

For subcloning the PS86A1(b) gene encoding the approximately 45 kDa toxin, preparative amounts of phage DNA were digested with EcoRV and SalI. The approximately 2.3 kbp band was ligated into SmaI+SalI-digested pHTBlueII. The ligation mix was used to transform frozen, competent *E. coli* NM522 cells (ATCC 47000). β-galactosidase-negative transformants were screened by restriction digestion of alkaline lysate plasmid miniprep DNA. The desired plasmid construct, pMYC2344, contains the PS86A1(b) toxin gene. pMYC2344 was introduced into the acrystalliferous (Cry−) *B.t.* host, CryB (A. Aronson, Purdue University, West Lafayette, Ind.) by electroporation. Expression of the toxin was demonstrated by visualization of crystal formation under microscopic examination, and SDS-PAGE analysis. Gene construct pMYC2344 in *B.t.* is designated MR509.

A sequence of the 86A1(b) gene is shown in SEQ ID NO.2. A deduced amino acid sequence for the 86A1(b) toxin is shown in SEQ ID NO. 3.

The PS86A1(b) probes, hybridization, and washing conditions were also used to clone a related gene, PS52A1(b), from *Bacillus thuritigiensis* strain PS52A1. A gene library was constructed by partially digesting PS52A1 total cellular DNA with Sau3A 1. Partial restriction digests were fractionated by agarose gel electrophoresis. DNA fragments 9.3 to 23 kbp in size were excised from the gel, electroeluted from the gel slice, purified on an Elutip-D ion exchange column, and recovered by ethanol precipitation. The Sau3A I inserts were ligated into BamHI-digested LambdaGem-11. Recombinant phage were packaged and plated on *E. coli* KW251 cells. Plaques were screened by hybridization with the PCR probe described previously. Hybridizing phage were plaque-purified and used to infect liquid cultures of *E. coli* KW251 cells for isolation of DNA by standard procedures. Southern blotting of plaque-purified hybridizing phage DNA digested with selected restriction endonucleases using the PCR probe revealed an approximately 2.3 kbp EcoRV+SalI fragment believed to contain the PS52A1(b) gene.

For subcloning the PS52A1(b) gene encoding the approximately 45 kDa toxin, preparative amounts of phage DNA were digested with EcoRV and SalI. The approximately 2.3 kbp band was ligated into SmaI+SalI-digested pHTBlueII. The ligation mix was used to transform frozen, competent *E. coli* NM522 cells. β-galactosidase-negative transformants were screened by restriction digestion of alkaline lysate plasmid miniprep DNA. The desired plasmid construct, pMYC2349, contains the 52A1(b) toxin gene that is novel compared to other toxin genes containing insecticidal proteins. pMYC2349 was introduced into the acrystalliferous (Cry−) *B.t.* host, CryB, by electroporation. Expression of the toxin was demonstrated by visualization of crystal formation under microscopic examination, and SDS-PAGE analysis. Gene construct pMYC2349 in *B.t.* is designated MR510.

A sequence of the 52A1(b) gene is shown in SEQ ID NO.4. A deduced amino acid sequence for the 52A1(b) toxin is shown in SEQ ID NO.5.

EXAMPLE 3

Bioassay of the MR509/86A1(b) Toxin Against Phyllotreta

Wild *Phyllotreta cruciferae* were collected and held in rearing chambers at 25° C., 16L:8D photoperiod. Five canola (Hyola 401) seeds were planted in standard potting soil. Cotyledons were excised from seedlings and dipped in *B.t.* MR509 suspensions (100 ug toxin/ml) made with 0.1% Bond (Bond served as a sticking agent). A single treated cotyledon was allowed to dry and was placed in a plastic well (NuTrend trays) containing approximately 1 ml of a 2% agar gel. The agar gel served as a moisture source to increase the longevity of the excised cotyledons. A single adult beetle was placed in each assay well. Assays were stored at room temperature. Mortality and plant damage was assessed at 4 and 7 days post treatment. Cotyledon damage was assessed on a 1–10 point scale with a scoring of 10 corresponding to complete destruction of plant tissue.

Several treatments showed reduced plant damage relative to untreated and CryB (a crystal-minus *B.t.* strain) controls. It was determined that the approximately 45 kda protein from MR509 was highly active against the tested *Phyllotreta cruciferae* pests; this toxin is referred to as the 86A1(b) gene.

EXAMPLE 4

Further Bioassays: MR509/86A1(b) and MR510/52A1(b) Against Phyllotreta spp.

MR509 and MR510 were evaluated in the following tests. CryB was used as a negative control. Other negative controls were untreated leaves and the Bond solution that was added as a spreader-sticker.

Newly sprouted cotyledons were excised and dipped in the test suspensions. After drying, the cotyledons were infested with 2 adult flea beetles. Leaf damage was assessed at 4 days post-infestation. Leaf damage was assessed on a scale of 0 to 10 with 0 being no damage.

The clones MR509 and MR510 gave clear indications of dose dependent leaf protection. This activity was particularly evident for MR510.

EXAMPLE 5

Truncations of the Native 86A1(b) and 52A1(b) Toxins

Using techniques known to those skilled in the art, some of which are discussed above, the native proteins can be truncated. These truncated toxins can be screened for activity by one skilled in the art using the guidance provided herein together with what is known in the art. Preferred, truncated proteins are shown in SEQ ID NOS. 8–19. The subject invention also includes polynucleotides that encode the exemplified, truncated proteins, as well as other truncations, fragments, and variants of the exemplified toxins, so long as the truncations, fragments, or variants retain pesticidal activity, preferably against coleopterans, and most preferably against flea beetles.

Truncated toxins according to the subject invention include not only toxins having deletions in the N-terminal or C-terminal portions as exemplified herein, but also toxins having deletions to both the N-terminal and C-terminal portions of the native protein. Examples of such truncations would include proteins resulting from using any of the N-terminal deletions exemplified herein together with any of the C-terminal deletions exemplified herein.

EXAMPLE 6

Further Characterization of 86A1(b) and 52A1(b) Toxins

A polyclonal antibody referred to as R#56 was developed and purified to the native toxin 52A1(b). This antibody recognizes the native 86A1(b) toxin. This antibody can be used in blotting screens (dot, slot, and/or western blots) to determine if homologs of the 52A1(b) and 86A1(b) toxins are present in other strains of Bacillus.

Thus, in further embodiment of the subject invention, additional pesticidal toxins can be characterized and/or identified by their level of reactivity with antibodies to pesticidal toxins exemplified herein. Antibodies can be raised to the specifically exemplified toxins of the subject invention. Other toxins within the scope of this invention can then be identified and/or characterized by their reactivity with the antibodies. In a preferred embodiment, the antibodies are polyclonal antibodies. In this embodiment, toxins with the greatest similarity to the 86A1(b) or 52A1(b) toxins would have the greatest reactivity with the polyclonal antibodies. Toxins with greater diversity react with polyclonal antibodies, but to a lesser extent.

EXAMPLE 7

Insertion of Toxin Genes Into Plants

One aspect of the subject invention is the transformation of plants with genes encoding the insecticidal toxin of the present invention. The transformed plants are resistant to attack by the target pest. Preferred genes will be stably maintained and expressed at high levels in the transformed plant and/or plant cells. An example of a preferred, synthetic, plant-optimized gene is provided in SEQ ID NO. 6, which is a dicot-optimized gene derived from MR510. The protein encoded by this gene is provided in SEQ ID NO. 7 (amino acid abbreviations are according to standard IUPAC conventions).

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the Bacillus toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable. It normally contains a selection marker that confers on the transformed plant cells resistance to a biocide, an herbicide such as glyphosate or BASTA, or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, micro-injection, biolistics (microparticle bombardment), PEG-mediated DNA uptake, or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as the host cell contains a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics, herbicides, or biocides for selection. The plants so obtained can then be tested for the presence of the inserted DNA. No special demands are made of the plasmids in the case of injection and electroporation. It is possible to use ordinary plasmids, such as, for example, pUC derivatives. In biolistic transformation, plasmid DNA or linear DNA can be employed.

The transformed cells are regenerated into morphologically normal plants in the usual manner. If a transformation event involves a germ line cell, then the inserted DNA and corresponding phenotypic trait(s) will be transmitted to progeny plants. Such plants can be grown in the normal manner and crossed with plants that have the same transformed hereditary factors or other hereditary factors. The resulting progeny plants have the corresponding phenotypic properties according to the rules of genetic segregation.

In a preferred embodiment of the subject invention, plants will be transformed with genes wherein the codon usaage has been optimized for plants. See, for example, U.S. Pat. No. 5,380,831. Also, advantageously, DNA encoding a truncated toxin will be used. The truncated toxin typically will encode about 55% to about 80% of the full length toxin. Methods for creating synthetic Bacillus genes for use in plants are known in the art.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An isolated protein that has toxin activity against a coleopteran pest wherein said protein has at least 95% identity with the amino acid sequence of SEQ ID NO:5.

2. The protein of claim 1 wherein said protein comprises the amino acid sequence of SEQ ID NO:5.

3. An isolated protein that has toxin activity against a coleopteran pest wherein said protein has at least 95% identity with a pesticidally active fragment of SEQ ID NO:5.

4. An isolated protein that has toxin activity against a coleopteran pest, wherein said protein is encoded by a polynucleotide wherein said polynucleotide hybridizes with the full complement of a nucleotide sequence that encodes the protein of SEQ ID NO:5 when said full complement is used as a hybridization probe, wherein hybridization is maintained at conditions of 0.1% SDS and 2×SSPE at room temperature.

5. The protein of claim 4 wherein hybridization is maintained at conditions of 0.1% SDS and 1×SSPE at room temperature.

6. The protein of claim 4 wherein hybridization is maintained at conditions of 0.1% SDS and 2×SSPE at 42° C.

7. The protein of claim 4 wherein hybridization is maintained at conditions of 0.1% SDS and 1×SSPE at 42° C.

8. The protein of claim 4 wherein hybridization is maintained at conditions of 0.1% SDS and 1×SSPE at 65° C.

9. The protein of claim 4 wherein hybridization is maintained at conditions of 0.1% SDS and 0.2×SSPE at 65° C.

10. The protein of claim 4 wherein hybridization is maintained at conditions of 0.1% SDS and 0.1×SSPE at 65° C.

* * * * *

UNITED STATES PATENT AND TRADEMARK OFFICE

CERTIFICATE OF CORRECTION

PATENT NO. : 6,710,027 B2 Page 1 of 1
DATED : March 23, 2004
INVENTOR(S) : Gregory Alan Bradfisch et al.

It is certified that error appears in the above-identified patent and that said Letters Patent is hereby corrected as shown below:

Column 1,
Line 10, "filed May 12 1999" should read -- filed May 12, 1998 --.

Column 17,
Line 46, "*thuritigiensis*" should read -- *thuringiensis* --.

Column 22,
Line 2, "usaage" should read -- usage --.

Signed and Sealed this

Fourteenth Day of September, 2004

JON W. DUDAS
*Director of the United States Patent and Trademark Office*